(12) United States Patent
Maier et al.

(10) Patent No.: US 7,038,037 B2
(45) Date of Patent: May 2, 2006

(54) METHOD FOR SEQUENTIAL SUPPORT-BOUND SYNTHESIS OF CONJUGATED OLIGOMERIC COMPOUNDS

(75) Inventors: Martin A. Maier, Carlsbad, CA (US); Andrei P. Guzaev, Carlsbad, CA (US); Muthiah Manoharan, Carlsbad, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 34 days.

(21) Appl. No.: 10/176,419

(22) Filed: Jun. 20, 2002

(65) Prior Publication Data
US 2004/0006203 A1 Jan. 8, 2004

(51) Int. Cl.
*C07H 21/00* (2006.01)
*C07H 21/02* (2006.01)
*C07H 21/04* (2006.01)

(52) U.S. Cl. .............................. 536/25.31; 536/25.31; 536/22.1; 536/23.1; 536/25.3; 536/25.6

(58) Field of Classification Search ................ 536/22.1, 536/23.1, 25.3, 25.6, 25.31
See application file for complete search history.

(56) References Cited

U.S. PATENT DOCUMENTS

| | | | |
|---|---|---|---|
| 5,539,082 A | 7/1996 | Nielsen et al. ............... | 530/300 |
| 5,700,922 A | 12/1997 | Cook ......................... | 536/23.1 |
| 5,719,262 A | 2/1998 | Buchardt et al. ............ | 530/300 |
| 6,506,594 B1 * | 1/2003 | Barany et al. ............ | 435/287.2 |

OTHER PUBLICATIONS

Zhou et al. Organic Letters (2000), vol. 2, pp. 3015-3018.*
Juby et al. Tetrahedron Letters (1991), vol. 32, pp. 879-882.*
Aldrian-Herrada, G., et al., "A peptide nucleic acid (PNA) is more rapidly internalized in cultured neurons when coupled to a *retro-inverso* delivery peptide. The antisense activity depresses the target mRNA and protein in magnocellular oxytocin neurons," *Nucleic Acids Res.*, 1998, 26(21), 4910-4916.
Antopolsky, M., et al., "Stepwise solid-phase synthesis of peptide-oligonucleotide phosphorothioate conjugates employing Fmoc peptide chemistry," *Tetrahedron Lett.*, 2000, 41, 9113-9117.
Antopolsky, M., et al., "Towards a general method for the stepwise solid-phase synthesis of peptide-oligonucleotide conjugates," *Tetrahedron Lett.*, 2002, 43, 527-530.
Ashwell, G., et al., "Carbohydrate-specific receptors of the liver," *Ann. Rev. Biochem*, 1982, 51, 531-554.
Basu, S., et al., "Synthesis and characterization of a peptide nucleic acid conjugated to a $_D$-peptide analog of insulin-like growth factor 1 for increased cellular uptake," *Bioconjugate Chem.*, 1997, 8, 481-488.

Basu, S., et al., "Solid phase synthesis of a $_D$-peptide-phosphorothioate oligodeoxynucleotide conjugate from two arms of a polyethylene glycol-polystyrene support," *Tetrahedron Lett.*, 1995, 36(28), 4943-4946.
Biessen, E.A.L., et al., "Synthesis of cluster galactosides with high affinity for the hepatic asialoglycoprotein receptor," *J. med. Chem.*, 1995, 38, 1538-1546.
Braasch, D.A., et al., "Novel antisense and peptide nucleic acid strategies for controlling gene expression," *Biochemistry*, Apr. 9, 2002, 41(14), 4503-4510.
Branden, L.J., et al., "A peptide nucleic acid-nuclear localization signal fusion that mediates nuclear transport of DNA," *Nat. Biotech.*, Aug. 1999, 17, 784-787.
Harrison, J.G., et al., "Inhibition of human telomerase by PNA-cationic peptide conjugates," *Bioorg. Med. Chem. Lett.*, 1999, 9, 1273-1278.
Hyrup, B., et al., "Peptide nucleic acids (PNA): synthesis, properties and potential applications," *Bioorganic & Medicinal Chem.*, 1996, 4(1), 5-23.
Judy, C.F., et al., "Facile preparation of 3' oligonucleotide-peptide conjugates," *Tetrahedron Lett.*, 1991, 32(7), 879-882.
Koch, T., et al., "PNA-peptide chimerae," *Tetrahedron Lett.*, 1995, 36(38), 6933-6936.
Lee, J.W., et al., "Reduction of azides to primary amines in substrates bearing labile ester functionality. Synthesis of a PEG-solubilized, "Y"-shaped iminodiacetic acid reagent for preparation of folate-tethered drugs," *Org. Lett.*, 1999, 1(2), 179-181.
Mayfield, L.D., et al., :Automated synthesis of peptide nucleic acids and peptide nucleic acid-peptide conjugates, *Anal. Biochem.*, 1999, 268, 401-404.
Pooga, M., et al., "Cell penetrating PNA constructs regulate galanin receptor levels and modify pain trasmission in vivo," *Nat. Biotech.*, 1998, 16, 857-861.
Simmons, C.G., et al., "Synthesis and membrane permaeability of PNA-peptide conjugates," *Bioorg. Med. Chem. Lett.*, 1997, 7(23), 3001-3006.
Schwabacher, A.W., et al., "Desymmetrization reactions: efficient preparation of unsymmetrically substituted linker molecules," *J. Org. Chem.*, 1998, 63, 1727-1729.
Zhou, X-T, et al., "Preparation of a protected triamino analogue of cholic acid and sequential incorporation of amino acids in solution and on a solid support," *Organic Letters*, 2000, 2(19), 3015-3018.

* cited by examiner

*Primary Examiner*—Patrick Lewis
(74) *Attorney, Agent, or Firm*—ISIS Patent Department Woodcock Washburn LLP

(57) ABSTRACT

A sequential support-bound synthesis method is disclosed for preparing a conjugated oligomeric compound, preferably a PNA-peptide conjugate or an oligonucleotide-peptide conjugate, using a bridging molecule having at least two N-protecting amino groups. A conjugated oligomeric compound for therapeutic or prophylactic delivery is also disclosed.

19 Claims, 5 Drawing Sheets

1. Removal of $R^1$
2. PNA solid phase synthesis

1. Blocking of amino terminus
2. Removal of $R^2$
3. Introduction of spacer unit
4. Attachment of target molecule (*e.g.*, fluorescent dye)

Cleavage from support medium, deprotection and evaluation of PNA

METHOD FOR SEQUENTIAL SUPPORT-BOUND SYNTHESIS OF CONJUGATED OLIGOMERIC COMPOUNDS

FIELD OF THE INVENTION

This invention is directed to a method for the sequential support-bound synthesis of conjugated oligomeric compounds, including peptide nucleic acid-peptide conjugates and oligonucleotide-peptide conjugates.

REFERENCE TO SEQUENCE LISTING

The attached Sequence Listing contains the sequences of the oligonucleotides and oligonucleotide mimetics of the invention and is incorporated herein by reference in its entirety.

BACKGROUND OF THE INVENTION

Peptide nucleic acid oligomers ("PNA") are nucleic acid analogs of DNA in which the sugar phosphodiester backbone has been replaced by a neutral, achiral polyamide (peptide) backbone having (2-aminoethyl) glycine carbonyl units linked to the purine or pyrimidine nucleobases through the glycine amino nitrogen and methylene carbonyl linkers (see, e.g., U.S. Pat. No. 5,539,082, the contents of which are incorporated herein by reference). PNAs have a high affinity for and hybridize to complementary RNA or DNA sequences by Watson-Crick base-pairing. Such hydridization is more rapid and more stable than hybridization between natural homoduplexes and possesses a greater potential for strand invasion because of the lack of electrostatic repulsion between the neutral PNA oligomers and the complementary RNA or DNA sequences. Furthermore, due to their altered backbone structures, PNAs are resistant to attack by nucleases and proteases. The chemical, physical and biological properties of PNAs make them useful, inter alia, as biomolecular tools, antisense and antigene agents, molecular probes and biosensors. For example, PNAs have been used to block protein expression on the transcriptional and translational level, monitor telomere length, inhibit human telomerase, affinity capture target nucleic acids, screen for genetic mutations, inhibit bacterial growth, and detect specific nucleic acid sequences in unamplified DNA.

In the case of antisense or antigene agents, one of the keys to their usefulness is that they must be taken up by the cells in a reasonable quantity so that they may reach their target in sufficient concentration. The uptake of oligonucleotides by cells, however, lacks efficiency. The uptake efficiency is particularly poor for PNAs because their neutral backbone linkages prevent effective transport across the cell membrane into the cytoplasm of the cell.

One of the known methods to improve PNA uptake into cells is to conjugate the PNA to a carrier molecule, such as DNA, cell-permeating peptide, peptidomimetic or other target molecule, to form a conjugate or chimera.

Oligonucleotide-peptide and PNA-peptide conjugates have been synthesized by sequential solid phase synthesis and by convergent synthesis in solution phase. Sequential solid phase synthesis of PNA-peptide conjugates is described by Simmons, C. G., Pitts, A. E., Mayfield, L. D., Shay, J. W., Corey, D. R. (1997) *Bioorg. Med. Chem. Lett,* 7, 3001–3006; Mayfield, L. D. and Corey, D. R. (1999) *Anal. Biochchem.,* 268, 401–404; Branden, L. J., Mohamed, A. J., Smith, C. I. E. (1999) *Nat. Biotech.,* 17, 784–787; Aldrian-Herrada, G., Desarmenien, M. G., Orcel, H., Boissin-Agasse, L., Mery, J., Brugidou, J., Rabie, A. (1998), *Nucleic Acids Res.,* 26, 4910–4916; Basu, S. and Wickstrom, E. (1997) *Bioconjugate Chem.,* 8, 481–488; Koch, T., et al. (1995) *Tetrahedron Lett.* 36, 6933–6936. Convergent synthesis in solution phase of PNA-peptide conjugates is described by Harrison, J. G., Frier, C., Laurant, R., Dennis, R., Raney, K. D., Balasubramanian, S. (1999) *Bioorg. Med. Chem. Lett.,* 9, 1273–1278; and Pooga, M., et al. (1998) *Nat. Biotech.,* 16, 857–861.

Both strategies have limited versatility and universal practical applicability. For the solid phase method, the outcome and quality of the synthesis of the conjugate are determined by the size and the solubility of the first entity on the solid support onto which the second entity is to be synthesized. For the solution phase conjugation method, separate step of purification of starting materials, synthesis and linking are required to form the conjugate. After conjugate formation, another purification step is required. Generally, the solution phase conjugation reaction is not quantitative and requires an excess of one of the entities to be conjugated. In some cases, the reaction requires a terminal cysteine to enable the formation of either a disulfide or thioether during the conjugation. Furthermore, no other cysteine units are permitted in the peptide.

Oligonucleotide-peptide conjugates have been prepared via the solid phase method using a bridging structure containing one protected hydroxy group for the oligonucleotide synthesis and one protected primary amino group for the peptide synthesis. See, for example, Juby, C. D., Richardson, C. D., Brousseau, R. (1991), *Tetrahedron Lett.* 32, 879–882; Basu, S., Wickstrom, E. (1995), *Tetrahedron Lett.,* 36, 4943–4946; Antopolsky, M., Azhayev, A. (2000) *Tetrahedron Lett.* 41, 9113–9117; Antopolsky, M.; Azhayeva, E., Tengvall, U., Azhayev, A. (2002) *Tetrahedron Lett.* 43, 527–530. Unfortunately, this approach has limited applicability because the peptide must be synthesized before the oligonucleotide is synthesized and the appropriate choice of amino acid side chain protection must be made.

Thus, there remains a need to maintain the advantages of solid phase synthesis, inter alia, facile removal of reagents and the ability the automate the process, and improve the synthesis if both entities to be ultimately conjugated (e.g., oligonucleotide or PNA with a peptide) independently of one another, by minimizing or eliminating the influence of the first entity on the synthesis of the second entity. The crux of applicants' invention lies the use of a bridging unit attached to a solid support that permits conjugation of at least two entities, such as PNAs or oligonucleotides with peptides, wherein the influence of one entity on the synthesis or attachment of the other entity(ies) is minimized or eliminated. The use of the special bridging unit does not introduce chiral or pro-chiral centers and provides a high degree of conformational flexibility. The improved synthesis method will enable new conjugated oligomeric compounds to be prepared with enhanced therapeutic, prophylactic, research and diagnostic potential.

BRIEF SUMMARY OF THE INVENTION

In one embodiment, the invention is directed to a method of preparing a conjugated oligomeric compound, preferably a PNA-peptide conjugate or an oligonucletoide-peptide conjugate, comprising the steps of:

providing a bridging unit bound to a support medium, said bridging unit comprising at least two orthogonally protected amino groups;

deblocking one of said at least two orthogonally protected amino groups and covalently attaching to said deblocked amino group a conjugate group or an oligomeric compound; and deblocking another of said at least two orthogonally protected amino groups and covalently attaching to said another deblocked amino group a conjugate group or an oligomeric compound;

wherein at least one conjugate group and at least one oligomeric compound are attached to said bridging unit. In certain embodiments, the covalently attaching step(s) is (are) carried out in a single step. In other embodiments, the covalently attaching step(s) is (are) carried out iteratively.

The method may further comprise the step of treating the conjugated oligomeric compound with a reagent effective to cleave it from the support medium. In addition, the method may further comprise the step of treating the conjugated oligomeric compound with a reagent effective to remove protecting groups.

In some preferred embodiments of the method, the conjugate group may be covalently attached to said bridging unit prior to attaching the oligomeric compound. In other preferred embodiments, the oligomeric compound may be covalently attached to said bridging unit prior to attaching said conjugate group.

In certain embodiments, the method may further comprise the step of covalently attaching a spacer unit to said another deblocked amino group and then covalently attaching said oligomeric compound to said spacer unit.

Preferably, the oligomeric compound is compound selected from the group consisting of an oligonucleotide, modified oligonucleotide, oligonucleotide analog, oligonucleoside.or oligonucleotide mimetic, such as a peptide nucleic acid or a morpholino-based oligomeric compound, hemimer, gapmer or inverted gapmer. Preferably, the oligomeric compound is iteratively synthesized using phosphoramidite chemistry.

Preferably, the conjugate group is selected from the group consisting of a receptor targeting moiety, intercalator, reporter molecule, crosslinking agent, cholesterol, peptide, polypeptide, polyamide, polyamine, amphipathic moiety, polyether, polycation group, lipophilic carrier, protein binder, carbohydrate, a carbohydrate cluster, and a vitamin. Preferably, the carbohydrate cluster has from 2 to about 5 carbohydrates selected from galactose and mannose. Preferably, the conjugate group is cholesterol, folic acid, a peptide, a polypeptide, ibuprofen, biotin or polyethyleneglycol Preferably, the peptide has a higher percentage of arginine than any other amino acid.

In certain preferred embodiments, the bridging unit comprises a moiety derived from lysine, 2-substituted malonodiamide, trisubstituted benzene, 3-hydroxyglutaric acid diamide, substituted iminodiacetic acid or a molecule of Formula X:

Formula X

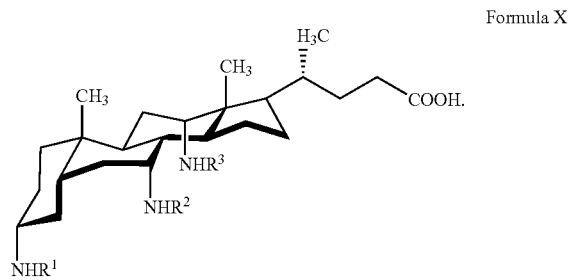

In other preferred embodiments, the bridging unit is free of a moiety of the structure:

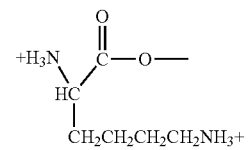

In certain preferred embodiments, the bridging unit is bound to the support medium by a linking unit, preferably a moiety derived from 5-(4'-aminomethyl-3',5'-dimethoxyphenoxy)valeric acid, 9-amino-xanthen-3-yloxy, thioester, trityl, 4-hydroxymethylbenzoic acid, or methylbenzhydrylamine.

In another embodiment, the invention is directed to a method of preparing a conjugated oligomeric compound comprising the steps of:

providing a bridging unit bound to a support medium, said bridging unit comprising at least two orthogonally protected amino groups;

deblocking one of said at least two orthogonally protected amino groups and covalently attaching a conjugate group to said deblocked amino group;

deblocking another of said at least two orthogonally protected amino groups and covalently attaching a spacer unit comprising a protected hydroxyl group to said another deblocked amino group;

deprotecting said protected hydroxyl group; and covalently attaching an oligomeric compound Preferably, the method further comprises the step of attaching a spacer unit to said further deblocked orthogonally protected amino group prior to covalently attaching said oligomeric compound. In certain preferred embodiments, the spacer unit is derived from a molecule selected from tetraalkylene glycol.

In certain embodiments of either method, the bridging unit may comprise at least three orthogonally protected amino groups and the method may further comprise the step of deblocking the third of said at least three orthogonally protected amino groups and covalently attaching a conjugate group or an oligomeric compound to said deblocked third amino group in a single step or by iterative synthesis. In other embodiments, the method further comprises the step of attaching a spacer unit, preferably derived from tetraalkylene glycol, to said deblocked third amino group and then covalently attaching said oligomeric compound to said spacer unit.

DETAILED DESCRIPTION OF THE INVENTION

Figure 1:
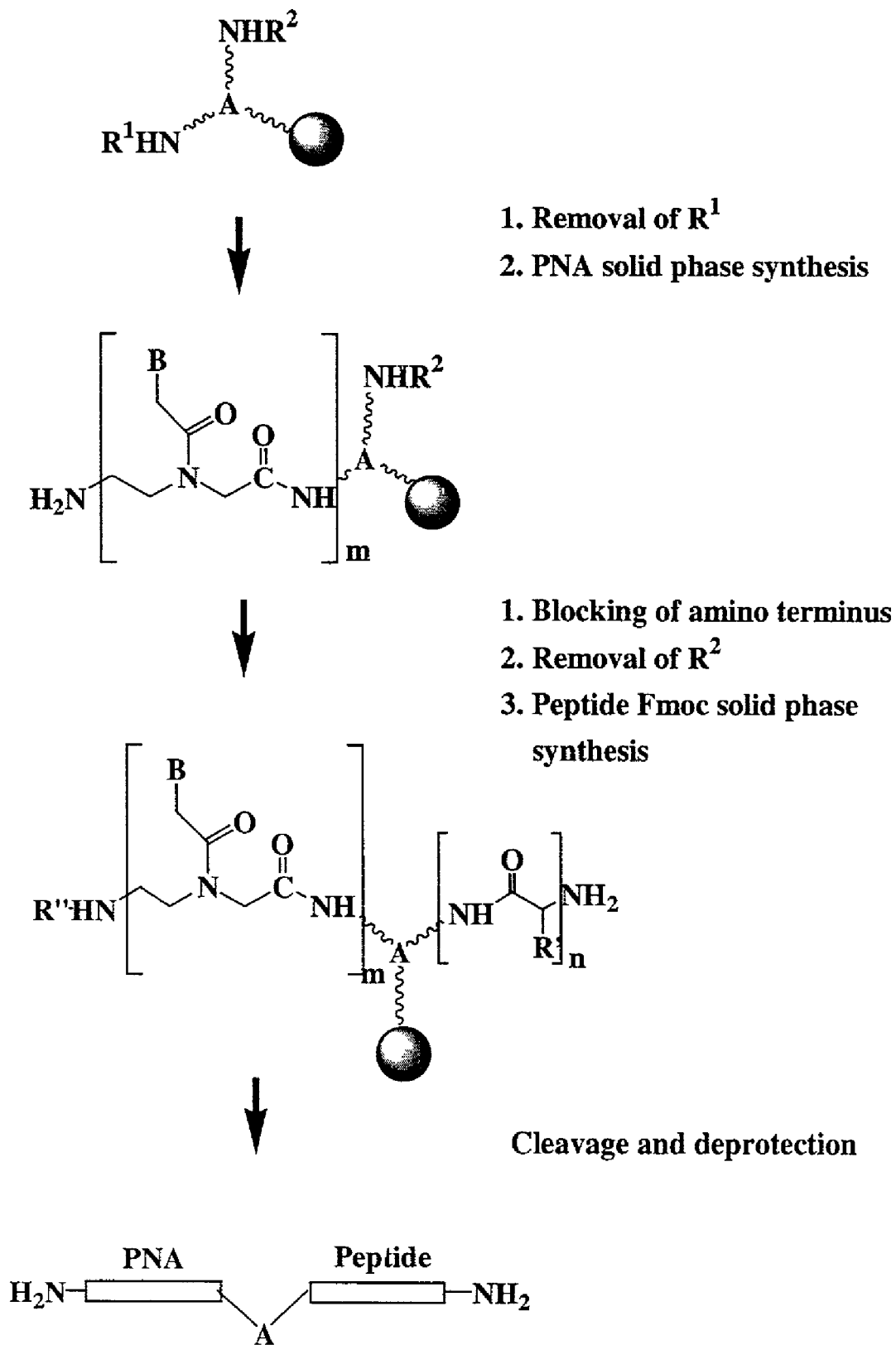
FIG. 1 is a schematic drawing of the solid phase synthesis of a PNA-peptide conjugate of the invention, wherein the PNA is synthesized first.

The present invention provides methods of preparing conjugated oligomeric compounds in a sequential manner using support based chemistries. The present methods enable preparation of the oligomeric compounds having covalently attached conjugate groups from bridging units that are bound to the support medium by an optional linking unit.

In the context of this invention, the term "oligomeric compound" refers to a polymeric structure capable of hybridizing a region of a nucleic acid molecule. This term includes oligonucleotides, oligonucleosides, oligonucleotide analogs, modified oligonucleotides and oligonucleotide mimetics. Oligomeric compounds can be prepared to be linear or circular and may include branching. They can be prepared single stranded or double stranded and may include overhangs. In general an oligomeric compound comprises a backbone of linked monomeric subunits where each linked monomeric subunit is directly or indirectly attached to a heterocyclic base moiety. The linkages joining the monomeric subunits, the monomeric subunits and the heterocyclic base moieties can be variable in structure giving rise to a plurality of motifs for the resulting oligomeric compounds including hemimers, gapmers and chimeras.

As is known in the art, a nucleoside is a base-sugar combination. The base portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond, however, open linear structures are generally preferred. Within the oligonucleotide structure, the phosphate groups are commonly referred to as forming the internucleoside linkages of the oligonucleotide. The normal internucleoside linkage of RNA and DNA is a 3' to 5' phosphodiester linkage.

In the context of this invention, the term "oligonucleotide" refers to an oligomer or polymer of ribonucleic acid (RNA) or deoxyribonucleic acid (DNA). This term includes oligonucleotides composed of naturally occurring nucleobases, sugars and covalent internucleoside linkages. The terms "oligonucleotide analog" and "modified oligonucleotide" refers to oligonucleotides that have one or more non-naturally occurring portions which function in a similar manner to oligonucleotides. Such modified or substituted oligonucleotides are often preferred over native forms because of desirable properties such as, for example, enhanced cellular uptake, enhanced affinity for nucleic acid target and increased stability in the presence of nucleases.

In the context of this invention, the term "oligonucleoside" refers to nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include but are not limited to siloxane, sulfide, sulfoxide, sulfone, acetyl, formacetyl, thioformacetyl, methylene formacetyl, thioformacetyl, alkeneyl, sulfamate; methyleneimino, methylenehydrazino, sulfonate, sulfonamide, amide and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In the context of this invention, the term "oligonucleotide mimetic" refers to an oligonucleotide wherein the backbone (both the sugar and the internucleotide linkage) of the nucleotide units has been replaced with novel groups. The heterocyclic base moieties are maintained for hybridization with appropriate nucleic acid target compounds. Oligonucleotide mimetics can also include modified and novel heterocyclic base moieties to enhance properties such as hybridization.

One oligonucleotide mimetic that has been shown to have excellent hybridization properties is peptide nucleic acid (PNA). The backbone in PNA compounds is two or more linked aminoethylglycine units that gives PNA an amide containing backbone. The heterocyclic base moieties are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497–1500.

Another class of oligonucleotide mimetic that has been studied is based on linked morpholino units having heterocyclic base moieties attached to the morpholino ring. There are a number of linking groups reported that are used to link the morpholino rings. A preferred class of linking groups was selected as being non-ionic. The non-ionic morpholino-based oligomeric compounds are less likely to have undesired interactions with cellular proteins (Dwaine A. Braasch and David R. Corey, *Biochemistry*, 2002, 41(14), 4503–4510). Morpholino-based oligomeric compounds are disclosed in U.S. Pat. No. 5,034,506, issued Jul. 23, 1991.

The oligomeric compounds in accordance with this invention preferably comprise from about 8 to about 80 monomeric subunits (i.e. from about 8 to about 80 linked nucleosides for oligonucleotide based compounds). Particularly preferred oligomeric compounds are from about 8 to about 50 monomeric subunits, even more preferably those comprising from about 12 to about 30 monomeric subunits.

Preferred modified internucleoside linkages include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' link Preferred oligonucleotides having inverted polarity comprise a single 3' to 3' linkage at the 3'-most internucleotide linkage i.e. a single inverted nucleoside residue that may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

In more preferred embodiments of the invention, oligomeric compounds have one or more phosphorothioate and/or heteroatom internucleoside linkages, in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester internucleotide linkage is represented as —O—P(=O)(OH)—O—$CH_2$—]. The MMI type internucleoside linkages are disclosed in the above referenced U.S. Pat. No. 5,489,677. Preferred amide internucleoside linkages are disclosed in the above referenced U.S. Pat. No. 5,602,240. Also preferred are morpholino-based and PNA oligonucleotide mimetics disclosed in above referenced U.S. Pat. Nos. 5,034,506, 5,539,082, 5,714,331 and 5,719,262.

Oligomeric compounds may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted C1 to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$$ONH_2$, and O($CH_2$)$_n$ON[($CH_2$)$_n$$CH_3$]$_2$, where n and m are from 1 to about 10. Other preferred oligomeric compounds comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486–504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethylamino-ethoxy-ethyl or 2'-DMAEOE), i.e., 2'-O—$CH_2$—O—$CH_2$—N($CH_3$)$_2$, also described in examples hereinafter.

Other preferred modifications include 2'-methoxy (2'-O—$CH_3$), 2'-aminopropoxy (2'-O$CH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Further representative substituent groups include groups of formula I or II:

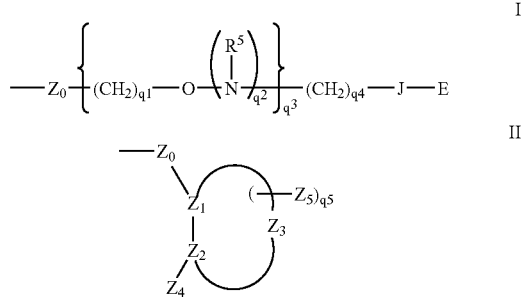

wherein:

$Z_0$ is O, S or NH;

J is a single bond, O or C(=O);

E is $C_1$–$C_{10}$ alkyl, N($R_5$)($R_6$), N($R_5$)($R_7$), N=C($R_{5a}$)($R_{6a}$), N=C($R_{5a}$)($R_{7a}$) or has Formula IV;

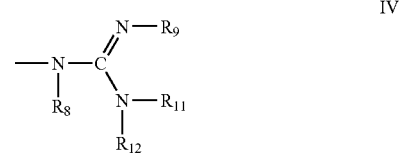

each $R_8$, $R_9$, $R_{11}$ and $R_{12}$ is, independently, hydrogen, C(O)$R_{13}$, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, $R_{11}$ and $R_{12}$, together form a phthalimido moiety with the nitrogen atom to which they are attached;

each $R_{13}$ is, independently, substituted or unsubstituted $C_1$–$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;

$R_5$ is T-L,

T is a bond or a linking moiety;

L is a chemical functional group, a conjugate group or a solid support material;

each $R_5$ and $R_6$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl and alkynyl. Further representative alkyl substituents are disclosed in U.S. Pat. No. 5,212,295, at column 12, lines 41–50, hereby incorporated by reference in its entirety.

or $R_5$ and $R_6$, together, are a nitrogen protecting group or are joined in a ring structure that optionally includes an additional heteroatom selected from N and O or a chemical functional group;

each $R_{5a}$ and $R_{6a}$ is, independently, H, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl and alkynyl. Further representative alkyl substituents are disclosed in U.S. Pat. No. 5,212,295, at column 12, lines 41–50, hereby incorporated by reference in its entirety.

$R_{7a}$ is -T-L;

each $R_{14}$ and $R_{15}$ is, independently, H, $C_1$–$C_{10}$ alkyl, a nitrogen protecting group, or $R_{14}$ and $R_{15}$, together, are a nitrogen protecting group;

or $R_{14}$ and $R_{15}$ are joined in a ring structure that optionally includes an additional heteroatom selected from N and O;

$Z_4$ is OX, SX, or $N(X)_2$;

each X is, independently, H, $C_1$–$C_8$ alkyl, $C_1$–$C_8$ haloalkyl, C(=NH)N(H)$R_{16}$, C(=O)N(H)$R_{16}$ or OC(=O)N(H)$R_{16}$;

$R_{16}$ is H or $C_1$–$C_8$ alkyl;

$Z_1$, $Z_2$ and $Z_3$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;

$Z_5$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_5)(R_6)$ $OR_5$, halo, $SR_5$ or CN;

each $q_1$ is, independently, an integer from 1 to 10;

each $q_2$ is, independently, 0 or 1;

$q_3$ is 0 or an integer from 1 to 10;

$q_4$ is an integer from 1 to 10;

$q_5$ is from 0, 1 or 2; and provided that when q3 is 0, q4 is greater than 1.

Representative substituents groups of Formula I are disclosed in U.S. patent application Ser. No. 09/130,973, filed Aug. 7, 1998, entitled "Capped 2'-Oxyethoxy Oligonucleotides," hereby incorporated by reference in its entirety.

Representative cyclic substituent groups of Formula II are disclosed in U.S. patent application Ser. No. 09/123,108, filed Jul. 27, 1998, entitled "RNA Targeted 2'-Modified Oligonucleotides that are Conformationally Preorganized," hereby incorporated by reference in its entirety.

Particularly preferred sugar substituent groups include O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10.

Representative guanidino substituent groups that are shown in formula III and IV are disclosed in co-owned U.S. patent application Ser. No. 09/349,040, entitled "Functionalized Oligomers", filed Jul. 7, 1999, hereby incorporated by reference in its entirety.

Representative acetamido substituent groups are disclosed in U.S. patent application Ser. No. 09/378,568, entitled "2'-O-Acetamido Modified Monomers and Oligomers", filed Aug. 19, 1999, hereby incorporated by reference in its entirety.

Representative dimethylaminoethyloxyethyl substituent groups are disclosed in International Patent Application PCT/US99/17895, entitled "2'-O-Dimethylaminoethyloxyethyl-Modified Oligonucleotides", filed Aug. 6, 1999, hereby incorporated by reference in its entirety.

A further preferred modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—CH$_2$—)$_n$ group bridging the 2' oxygen atom and the 4' carbon atom wherein n is 1 or 2. LNAs and their preparation are described in WO 98/39352 and WO 99/14226.

Oligomeric compounds may also include nucleobase (often referred to in the art simply as "base" or "heterocyclic base moiety") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyl-adenine, 5-propynyl-uracil and 5-propynyl-cytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications*, CRC Press, Boca Raton, 1993, pp. 276–278) and are presently preferred base substitutions, even more particularly when combined with 2'-O-methoxyethyl sugar modifications.

Further modified nucleobases include tricyclic heterocyclic base moieties such as for example 1,3,-diazaphenoxazine-2-one (1H-pyrimido[5,4-b][1,4]benzoxazin-2(3H)-one) and G-clamps such as 9-(2-aminoethoxy)-1,3,-diazaphenoxazine-2-one. Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,750,692; 5,830,653; 5,763,588; 6,005,096; and 5,681,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense oligomeric compounds which contain two or more chemically distinct regions, each made up of at least one monomer unit, i.e., a nucleotide in the case of an oligonucleotide compound. These oligomeric compounds typically contain at least one region modified so as to confer increased resistance to nuclease degradation, increased cellular uptake, and/or increased binding affinity for the target nucleic acid. An additional region of the oligomeric compound may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of inhibition of gene expression. Consequently, comparable results can often be obtained with shorter oligomeric compounds when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

Chimeric oligomeric compounds of the invention may be formed as composite structures of two or more oligonucleotides, modified oligonucleotides, oligonucleotide analogs, oligonucleosides and/or oligonucleotide mimetics as described above. Such compounds have also been referred to in the art as hybrids, hemimers, gapmers or inverted gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The present invention is directed to the synthesis of oligomeric compounds having at least one conjugate group covalently linked thereto. The covalent linkage of conjugate groups to oligomeric compounds has been shown to enhance properties such as for example a desired activity, cellular distribution and cellular uptake. Conjugate groups amenable to the present invention include any group capable enhancing one or more desired properties or capable of producing a desired effect when chemically linked to an oligomeric compound. Conjugate groups include but are not limited to peptides, ligand moieties, target molecules, lipid moieties such as intercalators, reporter molecules, polyamides, polyethers, lipids, biotin, phenazine, folate, glycoconjugate, phenanthridine, anthraquinone, acridine, fluoresceins, rhodamines, coumarins, dyes, a cholesterol moiety (Letsinger et al., *Proc. Natl. Acad. Sci. USA,* 1989, 86, 6553–6556), cholic acid (Manoharan et al., *Bioorg. Med. Chem. Let.,* 1994, 4, 1053–1060), a thioether, e.g., hexyl-S-tritylthiol (Manoharan et al., *Ann. N.Y. Acad. Sci.,* 1992, 660, 306–309; Manoharan et al., *Bioorg. Med. Chem. Let.,* 1993, 3, 2765–2770), a thiocholesterol (Oberhauser et al., *Nucl. Acids Res.,* 1992, 20, 533–538), an aliphatic chain, e.g., dodecandiol or undecyl residues (Saison-Behmoaras et al., *EMBO J.,* 1991, 10, 1111–1118; Kabanov et al., *FEBS Lett.,* 1990, 259, 327–330; Svinarchuk et al., *Biochimie,* 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651–3654; Shea et al., *Nucl. Acids Res.,* 1990, 18, 3777–3783), a polyamine or a polyethylene glycol chain (Manoharan et al., *Nucleosides & Nucleotides,* 1995, 14, 969–973), or adamantane acetic acid (Manoharan et al., *Tetrahedron Lett.,* 1995, 36, 3651–3654), a palmityl moiety (Mishra et al., *Biochim. Biophys. Acta,* 1995, 1264, 229–237), an octadecylamine or hexylamino-carbonyl-oxycholesterol moiety (Crooke et al., *J. Pharmacol. Exp. Ther.,* 1996, 277, 923–937), groups that enhance the pharmacodynamic properties of oligomeric compounds, and groups that enhance the pharmacokinetic properties of oligomers. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Further representative conjugate groups are disclosed in International Patent Application PCT/US92/09196, filed Oct. 23, 1992 the entire disclosure of which is incorporated herein by reference.

Conjugate groups amenable to the present invention include drug moieties that can in one embodiment enhance the uptake by binding to human serum albumin. Such drug moieties include, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in United States patent application Ser. No. 09/334,130 (filed Jun. 15, 1999), which is incorporated herein by reference in its entirety.

Representative United States patents that teach the use of the aforementioned conjugate groups include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582;

4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

In the context of this invention, the term "bridging unit" refers to a chemical compound having at least two orthogonally protected amino groups and a third functional group which is used directly or indirectly to attach a support medium. The bridging unit is first attached to a support medium that can be by an optional linking moiety. One of the orthogonally protected amino groups is deblocked and a conjugate group or an oligomeric compound is covalently attached. This can be accomplished in a single step as for the addition of for example an ibuprofen drug residue (ibuprofen has been shown bind to human serum albumin and enhance the uptake of oligonucleotides) or alternatively an iterative synthesis can be performed to covalently attach a conjugate group such as a peptide or an oligomeric compound such as a peptide nucleic acid. Another of the orthogonally protected amino groups is deblocked and a conjugate group or an oligomeric compound is covalently attached as discussed above.

Preferably, the bridging unit is designed such that cleavage at the end of the synthetic regime produces a C-terminal acid or amide. In preferred embodiments, a bridging unit containing an activated carboxyl group is keyed to amino groups on the solid support.

When an oligomeric compound such as an oligonucleotide or an oligonucleoside is covalently attached at one of the deblocked amino sites on the bridging unit a spacer unit is attached first. The spacer unit covalently attaches to the amino group and ends with a protected hydroxyl group. Deblocking the hydroxyl group gives a free hydroxyl that enables synthesis of oligomeric compounds using for example phosphoramidite chemistry. This method allows for multiple chemistries, such as, for example, Boc and Fmoc, chemistries at a first deblocked amino site on the bridging unit and then the chemistry is switched to one that would not have been compatible with the first by addition of the spacer unit. If a bridging unit were used having an amino and a hydroxyl group thereon the available chemistries would be much more limited.

As used herein, the term "peptide" refers to a compound comprising two or more amino acids joined by amide linkages formed between carboxyl and amino groups of respective amino acids. Preferred peptides include cellular permeation and translocation peptides, receptor-targeting peptides (such as RGD-peptides), peptoids and peptidomimetics.

A number of chemical functional groups can be introduced into compounds of the invention in a blocked form and subsequently deblocked to form a final, desired compound. Such as groups directly or indirectly attached at the heterocyclic bases, the internucleoside linkages and the sugar substituent groups at the 2', 3' and 5'-positions. Protecting groups can be selected to block functional groups located in a growing oligomeric compound during iterative synthesis while other positions can be selectively deblocked as needed. In general, a blocking group renders a chemical functionality of a larger molecule inert to specific reaction conditions and can later be removed from such functionality without substantially damaging the remainder of the molecule (Greene and Wuts, *Protective Groups in Organic Synthesis*, 3rd ed, John Wiley & Sons, New York, 1999). For example, the nitrogen atom of amino groups can be blocked as phthalimido groups, as 9-fluorenylmethoxycarbonyl (FMOC) groups, and with triphenylmethylsulfenyl, t-BOC or benzyl groups. Carboxyl groups can be blocked as acetyl groups. Representative hydroxyl protecting groups are described by Beaucage et al., *Tetrahedron* 1992, 48, 2223. Preferred hydroxyl protecting groups are acid-labile, such as the trityl, monomethoxytrityl, dimethoxytrityl, trimethoxytrityl, 9-phenylxanthine-9-yl (Pixyl) and 9-(p-methoxyphenyl)xanthine-9-yl (MOX).

Chemical functional groups can also be "blocked" by including them in a precursor form. Thus, an azido group can be used considered as a "blocked" form of an amine since the azido group is easily converted to the amine. Further representative protecting groups utilized in oligonucleotide synthesis are discussed in Agrawal, et al., *Protocols for Oligonucleotide Conjugates*, Eds, Humana Press; New Jersey, 1994; Vol. 26 pp. 1–72.

Examples of hydroxyl protecting groups include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p,p=-dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate.

Base labile amino-protecting groups that are stable to acid treatment are used to make reactive amino groups selectively available for substitution. Examples of such groups are the Fmoc (E. Atherton and R. C. Sheppard in The Peptides, S. Udenfriend, J. Meienhofer, Eds., Academic Press, Orlando, 1987, volume 9, p.1), and various substituted sulfonylethyl carbamates exemplified by the Nsc group (Samukov et al., *Tetrahedron Lett.*, 1994, 35:7821; Verhart and Tesser, *Rec. Trav. Chim. Pays-Bas,* 1987, 107:621).

Additional amino-protecting groups include but are not limited to, carbamate-protecting groups, such as 2-trimethylsilylethoxycarbonyl (Teoc), 1-methyl-1-(4-biphenylyl) ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

In some especially preferred embodiments, the nucleoside components of the oligomeric compounds are connected to each other by optionally protected phosphorothioate internucleoside linkages. Representative protecting groups for phosphorus containing internucleoside linkages such as phosphite, phosphodiester and phosphorothioate linages include β-cyanoethyl, diphenylsilylethyl, 6-cyanobutenyl, cyano p-xylyl (CPX), N-methyl-N-trifluoroacetyl ethyl (META), acetoxy phenoxy ethyl (APE) and butene-4-yl groups. See for example U.S. Pat. Nos. 4,725,677 and Re. 34,069 (β-cyanoethyl); Beaucage, S. L. and Iyer, R. P., *Tetrahedron,* 49 No. 10, pp. 1925–1963 (1993); Beaucage, S. L. and Iyer, R. P., *Tetrahedron,* 49 No. 46, pp. 10441–10488 (1993); Beaucage, S. L. and Iyer, R. P., *Tetrahedron,* 48 No. 12, pp. 2223–2311 (1992). Other representative phosphorus protecting groups include —$CH_2CH=CHCH_2CN$, para-$C_6H_4CH_2CN$, —$(CH_2)_{2-5}$-N (H)COCF$_3$, —CH$_2$CH$_2$Si(C$_6$H$_5$)$_2$CH$_2$, —CH$_2$CH$_2$N(CH$_3$)COCF$_3$ and others known in the art.

As used herein, the terms "orthogonal" and "orthogonal system", as they apply to protective groups, refer to a set of completely independent classes of protective groups, wherein each class of protective groups, wherein each class of protecting group can be removed in any order and in the presence of all other classes. See Barany, G. and Merrifield, R. B., *J. Am. Chem. Soc.,* 1977, 99, 7363; idem, 1980, 102, 3084. Orthogonal protection is widely used in for example automated oligonucleotide synthesis. A functional group is deblocked in the presence of one or more other protected functional groups which is not affected by the deblocking procedure. This deblocked functional group is reacted in some manner.

As used herein, the term "linking unit" refers to a short moiety that it is bifunctional and permits coupling between functionalities on the bridging unit and solid support.

As used herein, the term "peptide" refers to a compound of two or more amino acids where the α carboxyl group of one acid is bound to the α amino group of another amino acid and specifically includes cellular permeation and translocation peptides, receptor-targeting peptides (such as RGD-peptides), peptoids and peptidomimetics but does not include peptide nucleic acid.

As used herein, the term "peptide nucleic acid" or "PNA" refers to any nucleic acid analogs of DNA in which the sugar phosphodiester backbone has been replaced by a neutral, achiral polyamide (peptide) backbone having (2-aminoethyl) glycine carbonyl units linked to the purine or pyrimidine nucleobases through the glycine amino nitrogen and methylene carbonyl linking units.

As used herein, the term "oligonucleotide" refers to a polynucleotide formed from naturally occurring bases, such as purine and pyrimidine heterocycles, and furanyl groups joined by native phosphodiester bonds. This term effectively refers to naturally-occurring species or synthetic species formed from naturally-occurring subunits or their close homologues. The term "oligonucleotide" may also refer to moieties which have portions similar to naturally-occurring oligonucleotides but which have non-naturally occurring portions. Thus, oligonucleotides may have altered sugar moieties or inter-sugar linkages. Exemplary among these are the phosphorothioate and other sulfur-containing species that are known for use in the art. In accordance with some preferred embodiments, at least some of the phosphodiester bonds of the oligonucleotide have been substituted with a structure which functions to enhance the stability of the oligonucleotide or the ability of the oligonucleotide to penetrate into the region of cells where the viral RNA is located. It is preferred that such substitutions include phosphorothioate bonds, phosphotriesters, methyl phosphonate bonds, short chain alkyl or cycloalkyl structures or short chain heteroatomic or heterocyclic structures. Most preferred are CH$_2$—NH—O—CH$_2$, CH$_2$—N(CH$_3$)—O—CH$_2$, CH$_2$—O—N(CH$_3$)—CH$_2$, CH$_2$—N(CH$_3$)—N(CH$_3$)—CH$_2$ and O—N(CH$_3$)—CH$_2$—CH$_2$ structures where phosphodiester is O—P—O—CH$_2$. Also preferred are morpholino structures, such as those described in U.S. Pat. No. 5,034,506. In accordance with other preferred embodiments, the phosphodiester bonds are substituted with other structures which are, at once, substantially non-ionic and non-chiral, or with structures which are chiral and enantiomerically specific. Still other linkages include those disclosed in U.S. Pat. Nos. 5,223,618; 5,378,825; 5,610,289; 5,602,240; and U.S. application Ser. No. 903,160, filed Jun. 24, 1992, entitled "Heteroatomic Oligonucleoside Linkages;" all assigned to the assignee of this invention. Persons of ordinary skill in the art will be able to select other linkages for use in practice of the invention.

Oligonucleotides may also include species that include at least some modified base forms. Thus, purines and pyrimidines other than those normally found in nature may be so employed. For example, deaza or aza purines and pyrimidines may be used in place of naturally purine or pyrimidine bases and pyrimidine bases having substituent groups at the 5- or 6-positions; purine bases having altered or replacement substituent groups at the 2-, 6- or 8-positions are also provided in some aspects of the present invention. Similarly, modifications on the furanosyl portion of the nucleotide subunits may also be effected. Examples of such modifications are 2'-O-alkyl- and 2'-halogen-substituted nucleotides. Some specific examples of modifications at the 2' position of sugar moieties that are useful in the present invention are OH, SH, SCH$_3$, F, OCN, O(CH$_2$)$_n$NH$_2$, O(CH$_2$)$_n$CH$_3$ where n is from 1 to about 10; C$_1$ to C$_{10}$ low alkyl, substituted lower alkyl, alkaryl or aralkyl; Cl, Br, CN, CF$_3$, OCF$_3$, O—, S—, or N-alkyl; O—, S—, or N-alkenyl; SOCH$_3$, SO$_2$CH$_3$; ONO$_2$; NO$_2$; N$_3$; NH$_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. Sugar mimetics, such as cyclobutyls, may also be used in place of the pentofuranosyl group. Exemplary modifications are disclosed in U.S. application Ser. No. 463,358, filed Jan. 11, 1990, entitled "Compositions And Methods For Detecting And Modulating RNA Activity;" U.S. application Ser. No. 566,977, filed Aug. 13, 1990, entitled "Sugar Modified Oligonucleotides That Detect And Modulate Gene Expression;" U.S. Pat. No. 5,138,045; U.S. application Ser. No. 558,806, filed Jul. 27, 1991, entitled "Nuclease Resistant Pyrimidine Modified Oligonucleotides That Detect And Modulate Gene Expression;" and International Application No. PCT/US91/00243, filed Jan. 11, 1991, entitled "Compositions and Methods For Detecting And Modulating RNA Activity;" U.S. Pat. No. 5,212,295; U.S. application Ser. No. 814,961, filed Dec. 24, 1991, entitled "Gapped 2' Modified Phosphorothioate Oligonucleotides;" U.S. Pat. No. 5,359,044; and U.S. application Ser. No. 782,374, filed Dec. 24, 1991, entitled "Derivatized Oligonucleotides Having Improved Uptake & Other Properties," all assigned to the assignee of this invention. The disclosures of all of the above noted patent applications are incorporated herein by reference. Oligonucleotides may also contain other modifications consistent with the spirit of this invention. Such oligonucleotides are best described as being functionally interchangeable but yet structurally distinct from natural oligonucleotides. All such oligonucleotides are comprehended by this invention so long as they effectively function as subunits in the oligonucleotide. Thus, purine-containing oligonucleotide are oligonucleotides containing at least one purine base or analog thereof.

Oligonucleotides useful in the present invention may be naturally-occurring or synthetically-produced and may range in length from about 8 to about 50 nucleotides. In more preferred embodiments of the present invention, the oligonucleotides may be from 8 to 40 nucleotides in length. Most preferably, oligonucleotides useful in the present invention may be from 12 to about 20 nucleotides in length.

As used herein, the term "conjugate group" refers to a molecule that is desired to be attached to the conjugated oligomeric compounds of the invention not including PNAs and oligonucleotides.

As used herein, the terms "treatment" and "therapy" are used interchangeable herein and refer to: the prevention of infection or reinfection (prophylaxis), the prevention of symptoms of a disease of interest, or the reduction or elimination of symptoms of a disease of interest.

As used herein, the use in lists in methods or compositions of numbers and letters does not imply any specific sequence or priority, unless explicitly stated.

Methods of Forming Conjugated Oligomeric Compounds

In one embodiment, the invention is directed to a method of preparing a conjugated oligomeric compound, preferably a PNA-peptide conjugate or an oligonucletoide-peptide conjugate, comprising the steps of:

providing a bridging unit bound to a support medium, said bridging unit having at least two orthogonally protected amino groups thereon;

deblocking one of said at least two orthogonally protected amino groups and covalently attaching thereto a conjugate group or an oligomeric compound in a single step or by iterative synthesis; and deblocking another of said at least two orthogonally protected amino groups and covalently attaching thereto a conjugate group or an oligomeric compound in a single step or by iterative synthesis;

wherein at least one conjugate group and at least one oligomeric compound are attached to bridging unit.

The method may further comprise the step of treating the conjugated oligomeric compound with a reagent effective to cleave it from the support medium. In addition, the method may further comprise the step of treating the conjugated oligomeric compound with a reagent effective to remove any protecting groups.

In some preferred embodiments of the method, the conjugate group may be covalently attached to said bridging unit prior to attaching the oligomeric compound. In other preferred embodiments, the oligomeric compound may be covalently attached to said bridging unit prior to attaching said conjugate group.

In certain embodiments, the method may further comprise the step of covalently attaching a spacer unit to said another deblocked amino group followed by covalently attaching said oligomeric compound.

Preferably, the oligomeric compound is compound selected from the group consisting of an oligonucleotide, modified oligonucleotide, oligonucleotide analog, oligonucleoside or oligonucleotide mimetic, such as a peptide nucleic acid or a morpholino-based oligomeric compound, hemimer, gapmer or inverted gapmer. Preferably, the oligomeric compound is iteratively synthesized using phosphoramidite chemistry.

Preferably, the conjugate group is selected from the group consisting of a receptor targeting moiety, intercalator, reporter molecule, crosslinking agent, cholesterol, peptide, polypeptide, polyamide, polyamine, amphipathic moiety, polyether, polycation group, lipophilic carrier, protein binder, carbohydrate, a carbohydrate cluster, and a vitamin. Preferably, the carbohydrate cluster has from 2 to about 5 carbohydrates selected from galactose and mannose. Preferably, the conjugate group is cholesterol, folic acid, a peptide, a polypeptide, ibuprofen, biotin or polyethyleneglycol Preferably, the peptide has a higher percentage of arginine than any other amino acid present In certain preferred embodiments, the bridging unit comprises a moiety derived from a molecule selected from the group consisting of lysine, 2-substituted malonodiamide, trisubstituted benzene, 3-hydroxyglutaric acid diamide, substituted iminodiacetic acid and a molecule of Formula X:

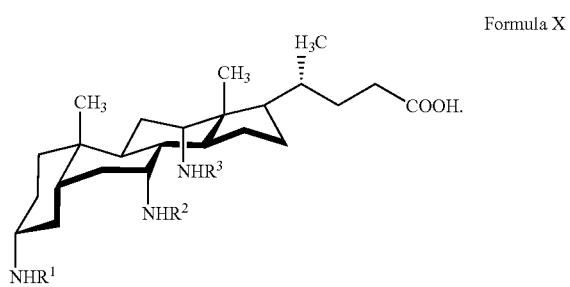

Formula X

In other preferred embodiments, the bridging unit is free of a moiety of the following structure:

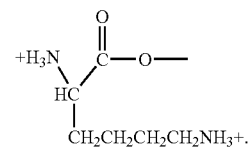

In certain preferred embodiments, the bridging unit is bound to the support medium by a linking unit, preferably a moiety derived from a molecule selected from the group consisting of 5-(4'-aminomethyl-3',5'-dimethoxyphenoxy) valeric acid, 9-amino-xanthen-3-yloxy, thioester, trityl, 4-hydroxymethylbenzoic acid and methylbenzhydrylamine.

The method of the invention may further comprise the step of deblocking a further of said at least two orthogonally protected amino groups and covalently attaching thereto a conjugate group or an oligomeric compound in a single step or by iterative synthesis.

In another embodiment, the invention is directed to a method of preparing a conjugated oligomeric compound comprising the steps of:

providing a bridging unit bound to a support medium, said bridging unit having at least two orthogonally protected amino groups thereon;

deblocking one of said at least two orthogonally protected amino groups and covalently attaching thereto a conjugate group in a single step or by iterative synthesis;

deblocking another of said at least two orthogonally protected amino groups and covalently attaching thereto a spacer unit having a protected hydroxyl group thereon;

deprotecting said protected hydroxyl group; and covalently attaching thereto an oligomeric compound by iterative synthesis. Preferably, the method further comprises the step of attaching a spacer unit to said further deblocked orthogonally protected amino group prior to covalently attaching said oligomeric compound. In certain preferred embodiments, the spacer unit is derived from a molecule selected from tetraalkylene glycol.

Support Media

The current method of choice for the preparation of oligomeric compounds utilizes support media. Support media is used for attachment of a first nucleoside or other synthon which is then iteratively elongated to give a final oligomeric compound or other polymer such as a polypeptide. Support media can be selected to be insoluble or have variable solubility in different solvents to allow the growing support bound polymer to be either in or out of solution as desired. Traditional support media such as solid supports are for the most part insoluble and are routinely placed in a reaction vessel while reagents and solvents react and or wash the growing chain until cleavage the final polymeric compound. More recent approaches have introduced soluble supports including soluble polymer supports to allow precipitating and dissolving the iteratively synthesized product at desired points in the synthesis (Gravert et al., *Chem. Rev.*, 1997, 97, 489–510).

The term "support media" is intended to include all forms of support known to the art skilled for the synthesis of oligomeric compounds and related compounds such as peptides. Some representative support media that are amenable to the methods of the present invention include but are not limited to the following: controlled pore glass (CPG); oxalyl-controlled pore glass (see, e.g., Alul, et al., *Nucleic Acids Research* 1991, 19, 1527); silica-containing particles, such as porous glass beads and silica gel such as that formed by the reaction of trichloro-[3-(4-chloromethyl)phenyl]propylsilane and porous glass beads (see Parr and Grohmann, *Angew. Chem. Internal. Ed.* 1972, 11, 314, sold under the trademark "PORASIL E" by Waters Associates, Framingham, Mass., USA); the mono ester of 1,4-dihydroxymethylbenzene and silica (see Bayer and Jung, *Tetrahedron Lett*, 1970, 4503, sold under the trademark "BIOPAK" by Waters Associates); TENTAGEL (see, e.g., Wright, et al., *Tetrahedron Letters* 1993, 34, 3373); cross-linked styrene/divinylbenzene copolymer beaded matrix or POROS, a copolymer of polystyrene/divinylbenzene (available from Perceptive Biosystems); soluble support media, polyethylene glycol PEG's (see Bonora et al., *Organic Process Research & Development*, 2000, 4, 225–231).

Further support media amenable to the present invention include without limitation PEPS support a polyethylene (PE) film with pendant long-chain polystyrene (PS) grafts (molecular weight on the order of $10^6$, (see Berg, et al., *J. Am. Chem. Soc.*, 1989, 111, 8024 and International Patent Application WO 90/02749),). The loading capacity of the film is as high as that of a beaded matrix with the additional flexibility to accomodate multiple syntheses simultaneously. The PEPS film may be fashioned in the form of discrete, labeled sheets, each serving as an individual compartment. During all the identical steps of the synthetic cycles, the sheets are kept together in a single reaction vessel to permit concurrent preparation of a multitude of peptides at a rate close to that of a single peptide by conventional methods. Also, experiments with other geometries of the PEPS polymer such as, for example, non-woven felt, knitted net, sticks or microwellplates have not indicated any limitations of the synthetic efficacy.

Further support media amenable to the present invention include without limitation particles based upon copolymers of dimethylacrylamide cross-linked with N,N'-bisacryloylethylenediamine, including a known amount of N-tertbutoxycarbonyl-beta-alanyl-N'-acryloylhexamethylenediamine. Several spacer molecules are typically added via the beta alanyl group, followed thereafter by the amino acid residue subunits. Also, the beta alanyl-containing monomer can be replaced with an acryloyl safcosine monomer during polymerization to form resin beads. The polymerization is followed by reaction of the beads with ethylenediamine to form resin particles that contain primary amines as the covalently linked functionality. The polyacrylamide-based supports are relatively more hydrophilic than are the polystyrene-based supports and are usually used with polar aprotic solvents including dimethylformamide, dimethylacetamide, N-methylpyrrolidone and the like (see Atherton, et al., *J. Am. Chem. Soc.*, 1975, 97, 6584, *Bioorg. Chem.* 1979, 8, 351, and J. C. S. Perkin 1538 (1981)).

Further support media amenable to the present invention include without limitation a composite of a resin and another material that is also substantially inert to the organic synthesis reaction conditions employed. One exemplary composite (see Scott, et al., *J. Chrom. Sci.*, 1971, 9, 577) utilizes glass particles coated with a hydrophobic, cross-linked styrene polymer containing reactive chloromethyl groups, and is supplied by Northgate Laboratories, Inc., of Hamden, Conn., USA. Another exemplary composite contains a core of fluorinated ethylene polymer onto which has been grafted polystyrene (see Kent and Merrifield, Israel *J. Chem.* 1978, 17, 243 and van Rietschoten in *Peptides* 1974, Y. Wolman, Ed., Wiley and Sons, New York, 1975, pp. 113–116). Contiguous solid supports other than PEPS, such as cotton sheets (Lebl and Eichler, *Peptide Res.* 1989, 2, 232) and hydroxypropylacrylate-coated polypropylene membranes (Daniels, et al., *Tetrahedron Lett.* 1989, 4345). Acrylic acid-grafted polyethylene-rods and 96-microtiter wells to immobilize the growing peptide chains and to perform the compartmentalized synthesis. (Geysen, et al., *Proc. Natl. Acad. Sci. USA*, 1984, 81, 3998). A "tea bag" containing traditionally-used polymer beads. (Houghten, *Proc. Natl. Acad. Sci. USA*, 1985, 82, 5131). Simultaneous use of two different supports with different densities (Tregear, *Chemistry and Biology of Peptides*, J. Meienhofer, ed., Ann Arbor Sci. Publ., Ann Arbor, 1972 pp. 175–178). Combining of reaction vessels via a manifold (Gorman, *Anal. Biochem.*, 1984, 136, 397). Multicolumn solid-phase synthesis (e.g., Krchnak, et al., *Int. J. Peptide Protein Res.*, 1989, 33, 209), and Holm and Meldal, in "Proceedings of the 20th European Peptide Symposium", G. Jung and E. Bayer, eds., Walter de Gruyter & Co., Berlin, 1989 pp. 208–210). Cellulose paper (Eichler, et al., *Collect. Czech. Chem. Commun.*, 1989, 54, 1746). Support mediated synthesis of peptides have also been reported (see, *Synthetic Peptides: A User's Guide*, Gregory A. Grant, Ed. Oxford University Press 1992; U.S. Pat. Nos. 4,415,732; 4,458,066; 4,500,707; 4,668,777; 4,973,679; 5,132,418; 4,725,677 and Re-34,069.)

Support bound oligonucleotide synthesis relies on sequential addition of nucleotides to one end of a growing chain. Typically, a first nucleoside (having protecting groups on any exocyclic amine functionalities present) is attached to an appropriate glass bead support and activated phosphite compounds (typically nucleotide phosphoramidites, also bearing appropriate protecting groups) are added stepwise to elongate the growing oligonucleotide. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. Nos. 4,725, 677 and Re. 34,069.

Commercially available equipment routinely used for the support media based synthesis of oligomeric compounds and related compounds is sold by several vendors including, for example, Applied Biosystems (Foster City, Calif.). Any other means for such synthesis known in the art may additionally or alternatively be employed. Suitable solid phase techniques, including automated synthesis techniques, are described in F. Eckstein (ed.), *Oligonucleotides and Analogues, A Practical Approach*, Oxford University Press, New York (1991).

One of the features that distinguishes the methods and conjugated oligomeric compounds of the present invention is the use, in the sequential solid phase synthesis of the conjugated oligomeric compounds on a support media, a special bridging unit covalently bound to a linking unit on a solid support. The bridging unit contains three arms or branches, two of which contain amino groups that are differently N-protected by $R^1$ and $R^2$ and one of which is capable of covalently bonding directly or indirectly to the solid support. The bridging unit is attached via an optional linking unit to the solid support. In certain embodiments, there is provided a bridging unit that contains four arms or branches, three of which contain amino groups that are differently N-protected by $R^1$, $R^2$ and $R^3$ and one of which is capable of covalently bonding directly or indirectly to the solid support. Each amino group has N-protection groups that differ significantly in reactivity under the sequential synthesis conditions, such that each amino group may be the connection point for the step-wise synthesis of a desired entity (e.g., peptide, PNA, oligonucleotide) or attachment of a desired entity (e.g., target molecule) of the conjugated oligomeric compound independently of the reaction of the other amino group(s).

Bridging Units with N-protected Amino Groups

The methods to synthesize the desired peptide, PNA or oligonucleotide that will become an entity in the conjugated oligomeric compound of the invention are conventional solid-phase syntheses well-known to those skilled in the art, with the utilization of the special bridging units containing at least two N-protected amino groups attached to a solid support as described herein.

Any of the several temporary or labile N-protecting amino protecting groups routinely used in the art are suitable for use in the temporary protection of the amino groups of the bridging unit of the present invention, provided they are selected such that any given N-protecting amino protecting group differs significantly, preferably acting as an orthogonal system, from any of the other N-protectingamino protecting groups of the other amino groups of the bridging unit of the invention. Preferred among these are the widely used tertiary butoxycarbonyl (Boc) and N-α-9-fluorenylmethyloxycarbonyl (Fmoc) groups. Other suitable amino protecting groups include allyloxycarbonyl (Alloc), 2-(4-biphenyl) propyl-2-biphenyl)propyl-2-oxycarbonyl (Bpoc), 2-(3,5,-dimethoxyphenyl) propyl-2-oxycarbonyl (Ddz), 1-(1-adamantyl)-1-methylethoxycarbonyl (Adpoc) and 4-methoxybenzyloxycarbonyl (Moz). Other suitable protecting groups will be apparent to those skilled in the art, based on their experience and knowledge and may be selected provided that they differ sufficiently in reactivity under the reaction conditions of the sequential solid phase support mediated synthesis used to prepare the conjugates of the invention. Preferably, the N-protecting amino protecting groups on the bridging unit form an orthogonal system, reacting under mutually exclusive reaction conditions, under the required sequential reaction conditions for the different synthesis schemes that must be completed to form the desired conjugate. For example, if a PNA-peptide conjugate is desired, then the N-protecting amino protecting groups must be selected such that under the reaction conditions to synthesize the PNA, where the first N-protecting amino protecting group is extracted from the first amino group, the second N-protecting amino protecting group on the second amino group will not also be extracted thereby undesirably permitting the second unprotected amino group to participate in the sequential reaction. Similarly, once the PNA entity has been added to the bridging unit, it must not be altered under the synthesis conditions used to form the peptide entity on the second amino group. This is also true when the peptide is to be synthesized first and the PNA is to be synthesized after the synthesis of the peptide has been completed.

Suitable examples of bridging units include moieties derived from lysine (Formula V), 2-substituted malonodiamide (Formula VI), trisubstituted benzene (Formula VII), 3-hydroxyglutaric acid diamide (Formula VIII), substituted iminodiacetic acid (Formula IX)(Lee, J. W. and Fuchs, P. L. (1999), *Org. Lett.* 1, 179–181) and triamine derivatives of cholic acid (Formula X) having the following structures:

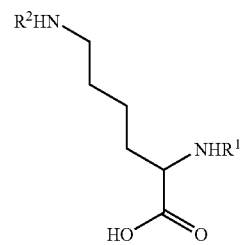

Formula V

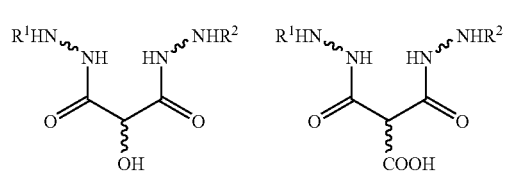

Formula VI

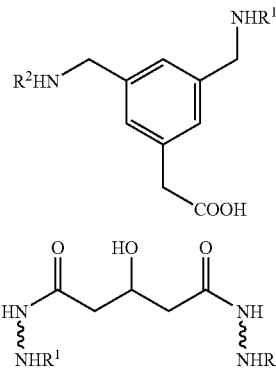

Formula VII

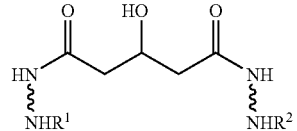

Formula VIII

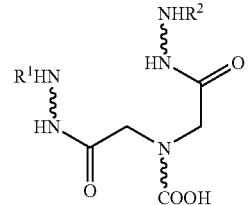

Formula IX

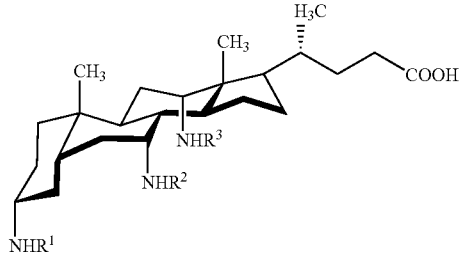

Formula X

The synthesis of bridging units of Formula IX may proceed as follows:

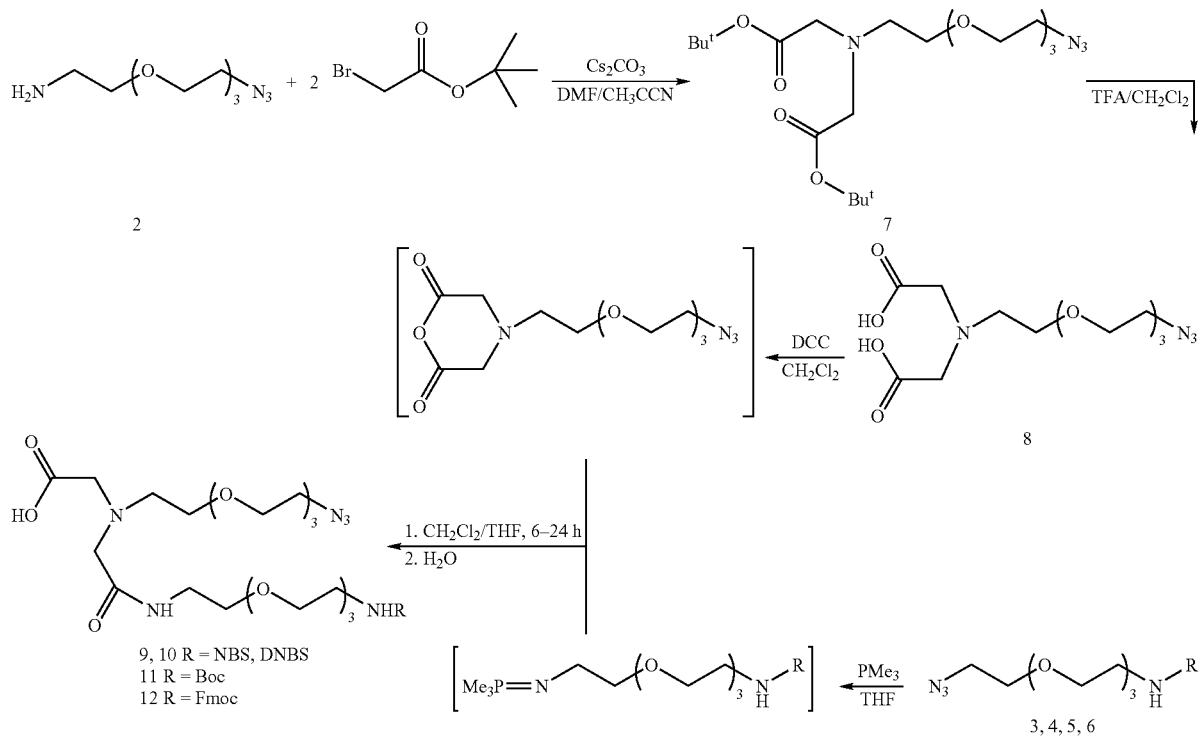

9, 10 R = NBS, DNBS
11 R = Boc
12 R = Fmoc 3, 4, 5, 6

This list is meant to be non-limiting in the sense that any moiety that contains at least two arms or branches, each of which contains an amino group that may be differently N-protected, preferably orthogonally, may be utilized. However, it is preferable that the bridging unit contains arms or branches of sufficient length and accessibility to permit the facile step-wise synthesis of the entities to be added to the bridging unit to form the conjugates of the invention. A particularly preferred bridging unit is:

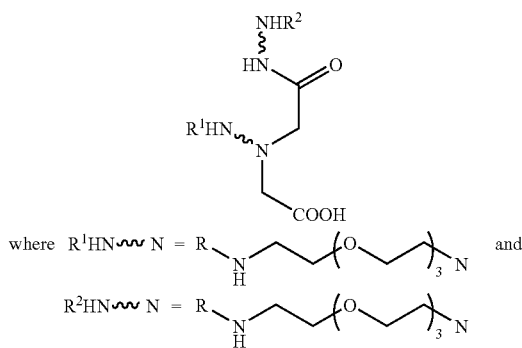

Optional Linking Units

More than fifty methods of using linking units to anchor the initial functionality to begin the chain growing reactions for the synthesis of the oligonucleotides, PNAs and peptides, to the solid phase support have been described. Many examples of covalently attaching a synthon to a support medium are documented in the literature. The present methods include an initial attachment of a bridging unit to a support medium by an optional linking moiety. Linking moieties used in traditional solid-phase peptide synthesis (see, e.g., Barany and Merrifield *The Peptides* Vol. 2, Academic Press, New York, 1979, pp. 1–284; Stewart and Young, *Solid Phase Peptide Synthesis,* 2nd Ed., Pierce Chemical Company, Illinois, 1984; *Oligonucleotides And Analogues A Practical Approach,* Ekstein, F. Ed., IRL Press, N.Y, 1991, Chapter 1, pages 1–23). Reactions for the introduction of linking units containing chloromethyl functionality (Merrifield resin; via a chloromethyl methyl ether/ $SnCl_4$ reaction), aminomethyl functionality (via an N-hydroxymethylphthalimide reaction; see, Mitchell, et al., *Tetrahedron Lett.,* 1976, 3795), and benzhydrylamino functionality (Pietta, et al., *J. Chem. Soc.,* 1970, 650) are the most widely applied. Regardless of its nature, the purpose of the linking unit is normally to form a connection between the solid support and bridging unit. Other reactive linking units that have been initially introduced include 4-methylbenzhydrylamino and 4-methoxy-benzhydrylamino. All of these established methods are in principle useful within the context of the present invention. Preferred methods employ aminomethyl as the initial functionality, in that aminomethyl is particularly advantageous with respect to the incorporation of the linking units, owing to the reactivity of the amino group of the aminomethyl functionality with respect to the essentially quantitative formation of amide bonds to a carboxylic acid group at one end of the linking unit-forming reagent.

A vast number of relevant linking unit-forming bifunctional reagents have been described (see, Barany, et al., *Int. J. Peptide Protein Res.,* 1987, 30, 705), especially reagents which are reactive towards amino groups, such as found in the aminomethyl function. Representative bifunctional reagents include 4–4-(haloalkyl)aryl-lower alkanoic acids such as 4-(bromomethyl)phenylacetic acid, Boc-aminoacyl-4-(oxymethyl)aryl-lower alkanoic acids such as Boc-aminoacyl-4-(oxymethyl)phenylacetic acid,N-Boc-p- N-Boc-p-acylbenzhydrylamines such as N-Boc-p-glutaroylbenzhydrylamine, N-Boc-4'-lowerN-Boc-4'-lower alkyl-p-acylbenzhydrylamines such as N—N-Boc-4'-methyl-p-glutaroylbenzhydrylamine, N-Boc-4'-lowerBoc-4'-methyl-p-glutaroylbenzhydrylamine, N-Boc-4'-lower alkoxy-p-acylbenzhydrylamines such as N-Boc-4'-methoxy-p-glutaroyl-benzhydrylamine,N-Boc-4'-methoxy-p-glutaroyl-benzhydrylamine, and 4-hydroxymethylphenoxyacetic acid. One type of linking unit particularly relevant within the context of the present invention is the phenylacetamidomethyl (Pam) handle (Mitchell and Merrifield, *J. Org. Chem.*, 1976, 41, 2015) which, deriving from the electron withdrawing effect of the 4-phenylacetamidomethyl group, is about 100 times more stable than the classical benzyl ester linkage towards the Boc-amino deprotection reagent trifluoroacetic acid (TFA).

A suitable linking unit includes one that is stable under the synthesis conditions but can be cleaved specifically after completion of the solid phase synthesis of the conjugated oligomeric compound. Other nonlimiting examples include moieties derived from 5-(4'-aminomethyl-3',5'-dimethoxyphenoxy) valeric acid, 9-amino-xanthen-3-yloxy, amino-xanthen-3-yloxy, thioester, trityl, thioester, trityl and 4-hydroxymethylbenzoic acid. Other suitable linking moieties include, but are not limited to, substituted or unsubstituted $C_1$–$C_{10}$ alkyl, substituted or unsubstituted $C_2$–$C_{10}$ alkenyl or substituted or unsubstituted $C_2$–$C_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl and alkynyl. Preferred linking moieties include hydrocarbyl chains and succinyl groups.

An alternative strategy concerning the introduction of linking unit is the so-called "preformed handle" strategy (see, Tam, et al., *Synthesis*, 1979, 955–957), which offers complete control over coupling of the bridging unit, and excludes the possibility of complications arising from the presence of undesired functional groups not related to the conjugate synthesis. In this strategy, linking units, of the same type as described above, are reacted with the bridging unit that is desired to bond to the solid support, the amino group of the bridging unit being N-protected and optionally protected at the other side-chains that are not relevant with respect to the growth of the desired entities. Thus, in those cases in which a linking unit is desirable, the bridging unit can either be coupled to the free reactive end of a linking unit that has been bound to the initially introduced functionality (for example, an aminomethyl group) or can be reacted with the linking unit-forming reagent. The linking unit-forming reagent is then reacted with the solid support. Other useful anchoring schemes include the "multidetachable" resins (Tam, et al., *Tetrahedron Lett.*, 1979, 4935 and *J. Am. Chem. Soc.*, 1980, 102,611; Tam, *J. Org. Chem.*, 1985,50,5291), which provide more than one mode of release and thereby allow more flexibility in synthetic design.

Figure 4:
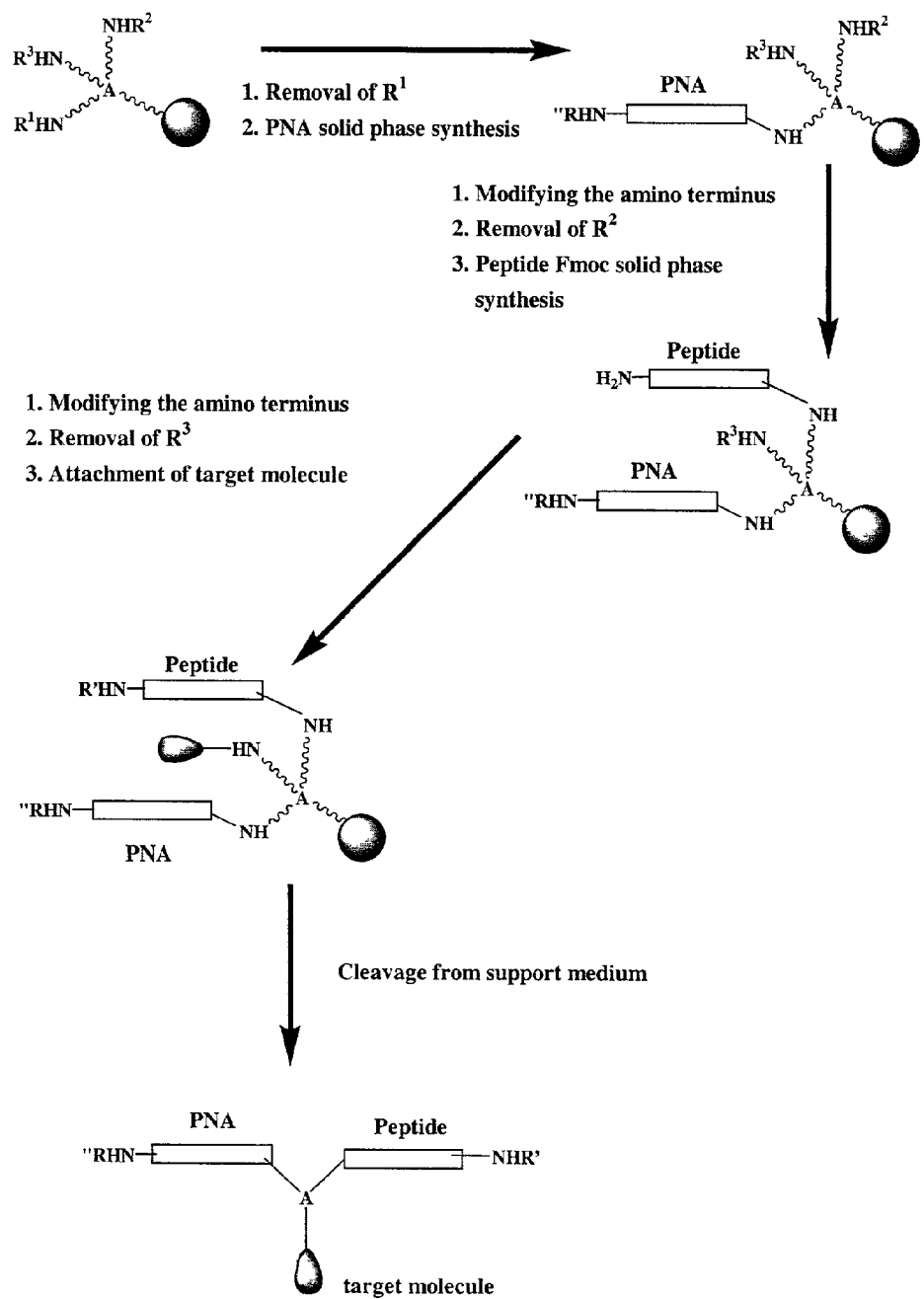
FIG. 4 is a schematic drawing of the solid phase synthesis of a PNA-target molecule-peptide conjugate of the invention.

In further embodiments, a conjugated oligomeric compound of the invention includes a third moiety that can be another conjugate group or another oligomeric compound. The synthesis of a PNA-target molecule-peptide conjugate is schematically shown in FIG. 4. Such synthesis is disclosed in Example 19 below where a support bound bridging unit having three orthogonally protected amino groups is sequentially reacted to give a final PNA-peptide conjugate that also includes another conjugate group, in this case a targeting moiety, attached to the bridging unit. Although we do not wish to be bound by theory, the inclusion of a third moiety is expected to enhance one or more additional properties of the final conjugated oligomeric compound. An oligomeric compound can be conjugated to two conjugate groups that both enhance its properties in a different way.

Figure 5:
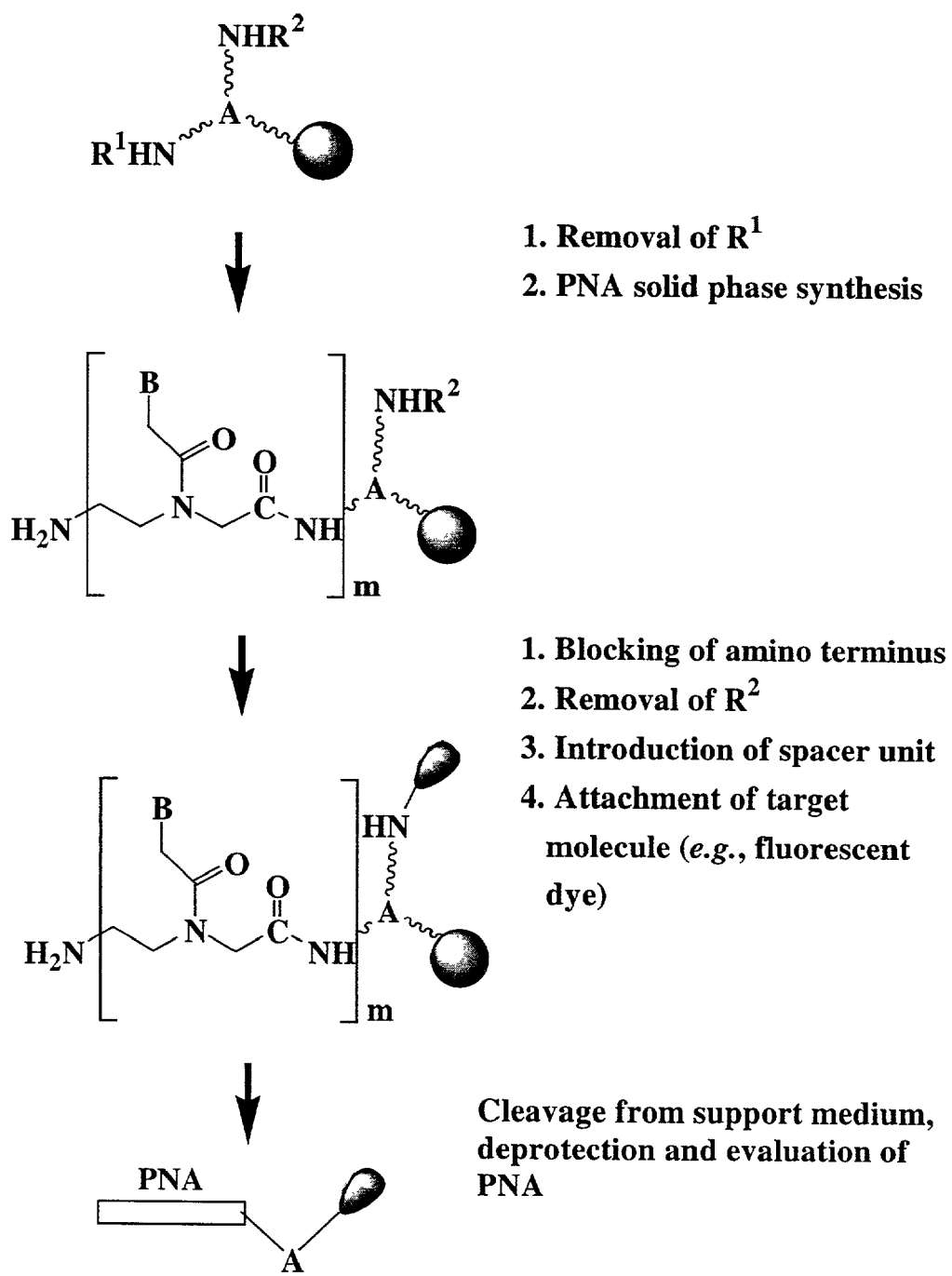
FIG. 5 is a schematic drawing of the solid phase synthesis of a target molecule-PNA conjugate, wherein the target molecule is a fluorescent dye for labeling, to permit evaluation of the PNA.

In other embodiments, a conjugate group-PNA conjugate may be formed, wherein the conhugate is a fluorescent dye for labeling, to permit evaluation of the PNA, as schematically shown in FIG. 5.

One of the conjugate groups can be a peptide that enhances the intracellular delivery of the oligomeric compound. This can be accomplished by covalently attaching a one of several types of "delivery peptides" that seem to have the ability to carry large, polar molecules including peptides, oligonucleotides, and even proteins across cell membranes (see: Schwarze, et al., *Trends Cell Biol.*, 2000, 10, 290–295; and Schwarze, et al., *Science* (Washington, D.C.), 1999, 285, 1569–1572). Two examples of delivery peptides are a 35-amino-acid sequence ("Tat") from the HIV Tat protein, and a 16-amino-acid sequence ("Ant") from the *Drosophila* Antennapedia protein. Antennapedia-type peptides have been used to deliver oligonucleotides, including PNAs, into neuronal cells. Other types of peptides, containing hydrophobic motifs and special recognition motifs, have also been used for antisense delivery.

Ant and Tat peptide-oligonucleotide conjugates have also been prepared for the MDR-1 system (see: Astriab-Fisher, et al., *Biochem. Pharmacol.*, 2000, 60, 83–90). The phosphorothioate oligonucleotide component of the conjugates was complementary to a site flanking the AUG of the message for P-glycoprotein, a membrane ATPase associated with multidrug resistance in tumor cells. Both types of peptide-antisense oligonucleotide conjugates, but not mismatched control conjugates, provided substantial inhibition (34%) of cell-surface expression of P-glycoprotein at submicromolar concentrations. The peptide-oligonucleotide conjugates were more potent in the presence of serum than when used under serum-free conditions which is in contrast to cationic lipid-based approaches for intracellular delivery of nucleic acids. Flow cytometry profiles indicated the conjugates accumulated in cells to a much greater degree than the free oligonucleotides. The conjugates reached the nucleus while the free oligonucleotides had virtually no intracellular fluorescence.

The second conjugate group can be selected to increase the serum uptake of the oligomeric compound thereby giving the oligomeric compound increased uptake and intracellular delivery simultaneously. Interaction of oligomeric compounds with proteins play an important role in absorption, distribution and pharmacokinetics. In the bloodstream, the major oligonucleotide binding protiens are immunoglobulins M and G, serum albumin, and orosomucoid-1-acid glycoprotein (AAG). The role of plasma protein binding is an important factor in oligonucleotide disposition and efficacy. If protein binding of oligonucleotides can be modulated with small molecular conjugation, it will result in more efficacious oligonucleotide drugs.

Albumin is a water-soluble protein with a molecular weight of 66,500 comprising a single chain of 585 amino acids containing a single tryptophan (Trp-214), low (2%) glycine content, high cystine content and a large number of charged amino acids (about 100 negative charges and 100 positive charges) and has an isoelectric point of about pH 5.0. Thus, at a plasma pH of 7.4, it has a net negative charge of −15. Nonetheless, it attracts both anions and cations. It circulates at a concentration of 3.5–5 g/100 mL in blood plasma and also exists at lower concentrations in extravascular fluids. About 60% of all human serum albumin (HSA) is located in the extravascular space (Peters, Adv. *Protein*

Chem., 1985, 37:161). As the most abundant protein in plasma, HSA plays an important role in the maintenance of blood pH and colloidal osmotic pressure and accounts for most of the thiol content of plasma (Cys-34). Binding of drugs to albumin is usually rapidly reversible. The binding (association) constants are typically in the range of $10^4$ to $10^6$ M$^{-1}$. HSA is organized in a series of three repeating domains (I, II and III) each having two subdomains. Conjugate groups such especially ligands bind to HSA generally to one or both of two binding sites. Site I is associated with the ligands warfarin, phenyl butazone. This site is localized in subdomain IIIA. Site II is in subdomain IIIA and binds to diazepam and ibuprofen. Other ibuprofen analogs, suprofen, pranoprofen, carprofen, fenbufen and ketoprofen, which are all non-steroidal antiinflammatory agents, bind to site II. Flufenamic acid and dansylsarcosine bind to site II while dansylamide binds to site I. Barbiturates such as quinalbarbitone interact with site II and the antidiabetic tolbutamide binds to site I, site II and an unidentified site. (R)-Folinic acid binds to both sites. Other compounds that bind to HSA include thiadiazides, diazepines, and antibacterials (e.g., nalidixic acid).

Lipoproteins can contribute to the plasma binding of lipophilic drugs and dissolve in lipid core of the lipoproteins. Cholesterol conjugated oligonucleotides are known to bind to serum proteins (see Agrawal et al., *Journal of Drug Targeting*, 1998, 5, 303–313) describe the effect of co-administration of aspirin at a concentration of 2 mg/mL and demonstrate that the P=S oligonucleotide binding to serum albumin is reduced (as measured by % protein bound of P=S oligonucleotide). This result indicates that presence of aspirin in the body or similar small molecule drugs could effectively alter protein binding of P=S oligonucleotides in vivo.

There are a multitude of combinations of conjugate groups that are envisioned by the present invention for use in conjugated oligomeric compounds having a third moiety. All that is required is the covalent attachment of one oligomeric compound at one of the deblocked amino functionalities. The order of attachment and the types of groups that can be attached are variable to accomodate chemistries in a logical order for best results.

Synthesis of Conjugated Entities

The iterative methods used to synthesize the desired moieties on each deblocked amino functionality including peptides, PNAs and oligomeric compounds such as oligonucleotides are performed using a bridging unit attached to a support medium using conventional solid-phase syntheses well-known to those skilled in the art.

These solid phase synthesis techniques utilize the ability to selectively protect and deprotect specific functional groupings. Protecting groups are conveniently characterized as either "temporary" or "permanent." "Temporary" or "labile" protecting groups are quantitatively removed at each step of the synthesis to allow coupling of the next synthon or monomer. "Permanent" or "stable" protecting groups are stable to the conditions of the iterative elongation cycle, and therefore protect side chain, nucleobase, or other functional groups which do not participate in, but may interfere with chain elongation. Typically, permanent protecting groups are chosen such that conditions required for their removal are equivalent to those required for cleavage of the completed chain from the reaction support, affording concomitant removal.

N-protecting groups are also necessary in the conventional synthesis of the peptides and PNAs. Suitable choices for N-protection of the growing peptide chains and PNA chains are the tert-butyloxycarbonyl (Boc) group (Carpino, *J. Am. Chem. Soc.*, 1957, 79, 4427; McKay, et al., *J. Am. Chem. Soc.*, 1957, 79, 4686; Anderson, et al., *J. Am. Chem. Soc.*, 1957, 79, 6180) normally in combination with benzyl-based groups for the protection of side chains, and the 9-fluorenylmethyloxycarbonyl (Fmoc) group (Carpino, et al., *J. Am. Chem. Soc.*, 1970, 92, 5748 and *J. Org. Chem.*, 1972, 37, 3404), normally in combination with tert-butyl (tBu) for the protection of any side chains, although a number of other possibilities exist which are well known in conventional solid-phase peptide synthesis. Thus, a wide range of other useful amino protecting groups exisst, some of which are Adoc (Hass, et al., *J. Am. Chem. Soc.*, 1966, 88, 1988), Bpoc (Sieber, *Helv. Chem. Acta.*, 1968, 51, 614), Mcb (Brady, et al., *J. Org. Chem.*, 1977, 42, 143), Bic (Kemp, et al., *Tetrahedron*, 1975, 4624), the o-nitrophenylsulfenyl (Nps) (Zervas, et al., *J. Am. Chem. Soc.*, 1963, 85, 3660), and the dithiasuccinoyl (Dts) (Barany, et al., *J. Am. Chem. Soc.*, 1977, 99, 7363). These amino protecting groups, particularly those based on the widely-used urethane functionality, successfully prohibit racemization (mediated by tautomerization of the readily formed oxazolinone (azlactone) intermediates) (Goodman, et al., *J. Am. Chem. Soc.*, 1964, 86, 2918)) during the coupling of α-amino acids. In addition to such amino protecting groups, a whole range of otherwise "worthless" nonurethane-type of amino protecting groups is applicable when assembling peptide and PNA molecules, especially those built from achiral units. Thus, not only the above-mentioned amino protecting groups (or those derived from any of these groups) are useful within the context of the present invention, but virtually any amino protecting group which largely fulfills the following requirements:

(1) stability to mild acids (not significantly attacked by carboxyl groups);

(2) stability to mild bases or nucleophiles (not significantly attacked by the amino group in question);

(3) resistance to acylation (not significantly attacked by activated amino acids). Additionally:

(4) the protecting group must be close to quantitatively removable, without serious side reactions; and (5) the optical integrity, if any, of the incoming amino acid should preferably be highly preserved upon coupling.

Finally, the choice of side-chain protecting groups, in general, depends on the choice of the amino protecting group, since the protection of side-chain functionalities must withstand the conditions of the repeated amino deprotection cycles. This is true whether the overall strategy for chemically assembling PNA molecules relies on, for example, differential acid stability of amino and side-chain protecting groups (such as is the case for the above-mentioned "Boc-benzyl" approach) or employs an orthogonal, that is, chemoselective, protection scheme (such as is the case for the above-mentioned "Fmoc-tBu" approach).

Synthesis of Peptide Entity

The methods of the present invention may be used to synthesize peptides by standard solid phase peptide synthesis (SPPS) methodologies (see, e.g., Merrifield, *J. Am. Chem. Soc.*, 1963, 85, 2149 and *Science*, 1986, 232, 341). Typically, SPPS is performed in the "C to N" direction. Preferably, the bridging unit is designed such that cleavage at the end of the synthetic regime produces a C-terminal acid or amide. In preferred embodiments, a bridging unit containing an activated carboxyl group is keyed to amino groups on the solid support.

Any of the several "temporary" protecting groups that routinely used in the art are suitable for use in the present invention. Preferred among these are the widely used BOC (t-butoxycarbonyl) and FMOC(N-α-9-fluorenylmethyloxycarbonyl) groups. Other suitable amino protecting groups include allyloxycarbonyl (Alloc), 2-(4-biphenyl)propyl-2-oxycarbonyl (Bpoc), 2-(3,5,-dimethoxyphenyl) propyl-2-oxycarbonyl (Ddz), 1-(1-adamantyl)-1-methylethoxycarbonyl (Adpoc) and 4-methoxybenzyloxycarbonyl (Moz). Other suitable protecting groups will be apparent to those skilled in the art, based on their experience and knowledge.

After coupling of the first monomeric synthon to the bridging unit, the iterative process of chain elongation occurs. This may proceed, in accordance with the invention, by any of the several methods known in the art for the formation of peptide bonds. Representative of such methods are the use of in situ coupling reagents, active esters, preformed symmetrical anhydrides and acid halides.

Representative in situ coupling reagents suitable for use in the present invention include N,N'-dicyclohexylcarbodiimide (DCC), and N,N'-diisopropylcarbodiimide (DIPCDI), especially in conjunction with the use of scavenging agents (so called accelerators or additives) such as 1-hydroxybenzotriazole (HOBt), benzotriazol-1-yl-oxy-tris (dimethylamino)phosphonium hexafluorophosphate (BOP), and 2-(1H-benzotriazol-1-yl)-1,1,3,3-tetramethyluronium hexafluorophosphate (HBTU). A list of suitable in situ coupling agents may be found in *Synthetic Peptides: A Users Guide*, supra.

Temporary protecting group on the terminal synthon is cleaved by adding a deprotection reagent and optionally a conventional rinsing reagent. The next protected monomeric synthon is then added in a suitable solvent, such as dimethyl formamide. Coupling or activating agents, including accelerators or additives such as HOBt, optionally may be added with the protected monomeric synthon or alternatively may be added independently in an appropriate solvent.

After a suitable reaction time, the iterative cycle is repeated until the desired amino acid sequence is achieved.

Synthesis of PNA Entity

The PNA oligomeric entities useful in the method and conjugated oligomeric compounds of the invention may be prepared generally in accordance with the methods disclosed by WO 92/20702. In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497–1500.

Peptide nucleic acids (PNAs) are prepared in accordance with any of the various procedures referred to in Peptide Nucleic Acids (PNA): Synthesis, Properties and Potential Applications, Bioorganic & Medicinal Chemistry, 1996, 4, 5–23. They may also be prepared in accordance with U.S. Pat. Nos. 5,539,082, 5,700,922, and 5,719,262, herein incorporated by reference.

PNA binds both DNA and RNA to form PNA/DNA or PNA/RNA duplexes. The resulting PNA/DNA or PNA/RNA duplexes are bound with greater affinity than corresponding DNA/DNA or DNA/RNA duplexes as determined by Tm's. This high thermal stability might be attributed to the lack of charge repulsion due to the neutral backbone in PNA. The neutral backbone of the PNA also results in the Tm's of PNA/DNA(RNA) duplex being practically independent of the salt concentration. Thus the PNA/DNA duplex interaction offers a further advantage over DNA/DNA duplex interactions which are highly dependent on ionic strength. Homopyrimidine PNAs have been shown to bind complementary DNA or RNA forming (PNA)2/DNA(RNA) triplexes of high thermal stability (see, e.g., Egholm, et al., Science, 1991, 254, 1497; Egholm, et al., J. Am. Chem. Soc., 1992, 114, 1895; Egholm, et al., J. Am. Chem. Soc., 1992, 114, 9677).

The binding of a PNA strand to a DNA or RNA strand can occur in one of two orientations. The orientation is said to be anti-parallel when the DNA or RNA strand in a 5' to 3' orientation binds to the complementary PNA strand such that the carboxyl end of the PNA is directed towards the 5' end of the DNA or RNA and amino end of the PNA is directed towards the 3' end of the DNA or RNA. In the parallel orientation the carboxyl end and amino end of the PNA are just the reverse with respect to the 5'-3' direction of the DNA or RNA.

PNAs bind to both single stranded DNA and double stranded DNA. As noted above, in binding to double stranded DNA it has been observed that two strands of PNA can bind to the DNA. While PNA/DNA duplexes are stable in the antiparallel configuration, it was previously believed that the parallel orientation is preferred for $(PNA)_2$/DNA triplexes.

The binding of two single stranded pyrimidine PNAs to a double stranded DNA has been shown to take place via strand displacement, rather than conventional triple helix formation as observed with triplexing oligonucleotides. When PNAs strand invade double stranded DNA, one strand of the DNA is displaced and forms a loop on the side of the $PNA_2$/DNA complex area. The other strand of the DNA is locked up in the $(PNA)_2$/DNA triplex structure. The loop area (alternately referenced as a D loop) being single stranded, is susceptible to cleavage by enzymes that can cleave single stranded DNA.

A further advantage of PNA compared to oligonucleotides is that their polyamide backbone (having appropriate nucleobases or other side chain groups attached thereto) is not recognized by either nucleases or proteases and are not cleaved. As a result PNAs are resistant to degradation by enzymes unlike DNA and peptides.

Because of their properties, PNA are known to be useful in a number of different areas. Since PNAs having stronger binding and greater specificity than oligonucleotides, they are used as probes in cloning, blotting procedures, and in applications such as fluorescence in situ hybridization (FISH). Homopyrimidine PNAs are used for strand displacement in homopurine targets. The restriction sites that overlap with or are adjacent to the D-loop will not be cleaved by restriction enzymes. Also, the local triplex inhibits gene transcription. Thus in binding of PNAs to specific restriction sites within a DNA fragment, cleavage at those sites can be inhibited. Advantage can be taken of this in cloning and subcloning procedures. Labeled PNAs are also used to directly map DNA molecules. In effecting this, PNA molecules having a fluorescent label are hybridized to complementary sequences in duplex DNA using strand invasion.

In accordance with this invention, it has been found that the most stable triplexes that are formed between two single stranded PNAs or a bis PNA and a DNA or RNA target strand are triplexes wherein the Watson/Crick base pairing strand is in an anti-parallel orientation relative to the target strand and the Hoogsteen base pairing strand is in a parallel orientation relative to the target strand. As so orientated to the target strand, the two PNA strands are therefore anti-parallel to each other.

Bis PNAs have shown improved binding affinity, thermal stability, and specificity over single stranded PNAs. Using dsDNA as a target it has been shown that the preferred orientation is with the first PNA strand of the bis PNA parallel to the target, i.e. the target DNA strand of the duplex is referenced in a 5' to 3' direction and the first PNA is complementary in an N to C direction, and the second PNA strand of the bis PNA is antiparallel to the target, i.e. it is complementary to the DNA strand (again referenced in a 5' to 3' direction) in a C to N direction. Thus the linking segment connects the PNA strands in opposite orientation to each other, i.e. from a common reference point, one strand is lined up in a N to C direction and the other is lined up in a C to N direction.

Although we do not wish to be bound by theory it is believed that the antiparallel strand of the bis PNA binds the DNA target thereby displacing the other DNA strand via strand invasion. This binding is of a Watson/Crick nature. The second PNA strand of the bis PNA, the parallel strand, now binds the DNA using Hoogsteen type hydrogen bonding. It has been shown using the component single stranded PNAs and comparing them separately and as a mixture to the bis PNA that the bis PNA has a faster on rate e.g. it binds faster to the target. This faster on rate is attributed to the enforced close proximity of the second strand in the bis PNA.

We have also studied the effect of pH on the Tm of bis PNA bound to dsDNA as compared to the same bis PNA with the cytosines replaced with pseudo isocytosines. It has been observed in previous studies that there is a pronounced dependence on pH for binding of PNA to dsDNA. The decrease in Tm with higher pH shows that Hoogsteen binding in a (PNA)$_2$/DNA complex is pH dependent. Normal Hoogsteen binding requires that the cytosines be protonated. This makes the Hoogsteen strand binding pH dependent. We have found that replacement of one or more of the cytosine nucleobases in a Hoogsteen strand with pseudo isocytosine and other like nucleobases removes this dependence. To demonstrate this effect, in two bis PNAs of the invention, one was synthesized such that the cytosines nucleobases in the parallel strand were replaced with pseudo isocytosines and the other was synthesized such that the cytosines in the antiparallel strand were replaced with pseudo isocytosines. The bis PNA with the pseudo isocytosines in the parallel strand showed almost no dependence on pH indicating that the parallel strand is involved with Hoogsteen binding.

The replacement of cytosine by pseudo isocytosine or other like C-pyrimidine nucleobases is effected in a straight forward manner as per certain of the examples set forth below. This is in direct contrast with replacement of cytosine with pseudo isocytosine or other C-pyrimidines in nucleosides. In nucleosides, an anomeric specific carbon-carbon bond must be formed in synthesizing the C-nucleoside. Since there are no anomeric (sugar) carbon atoms in peptide nucleic acids, such constraints need not be considered.

The triple helix principle is used in the art for sequence-specific recognition of dsDNA. Triple helix formation utilizes recognition of homopurine-homopyrimidine sequences. A strand displacement complex with triple helix formation is superior to simple triple helix recognition in that strand displacement complexes are very stable at physiological conditions, that is, neutral pH, ambient (20–40 □C) temperature and medium (100–150 mM) ionic strength.

Sequence-specific recognition of ssDNA by base complementary hybridization can likewise be exploited to target specific genes and viruses. In this case, the target sequence is contained in the mRNA such that binding of the drug to the target hinders the action of ribosomes and, consequently, translation of the mRNA into protein. The bis PNAs of the invention are superior to prior reagents in that they have significantly higher affinity for complementary ssDNA. Also, they can be synthesized such that they possess no charge and are water soluble, which should facilitate cellular uptake, and they contain amides of non-biological amino acids, which should make them biostable and resistant to enzymatic degradation by, for example, proteases.

The following abbreviations are used in the experimental examples: egl, —NH—CH$_2$—CH$_2$—O—CH$_2$—CH$_2$—O—CH$_2$—C(=O)—; Aha, 6-amino hexanoic acid; DMF, N,N-dimethylformamide; DCC, N,N-dicyclohexyl carbodiimide; DCU, N,N-dicyclohexyl urea; THF, tetrahydrofuran; aeg, (2'-aminoethyl)glycine.

Modification of the PNA backbone is also amenable to the present invention. In one embodiment the methylene group of the glycyl portion of the aminoethyl glycyl backbone is substituted with a functional group. The resulting PNA oligomer has the formula:

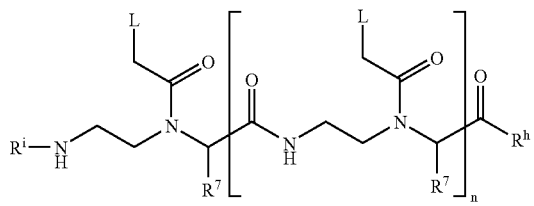

wherein:
  each L is, independently, a heterocyclic base moiety;
  each $R^7$ is, independently, hydrogen or $C_1$–$C_8$ alkylamine;
  $R^h$ is OH, NH$_2$ a protected amino group or NHLysNH$_2$;
  $R^i$ is H, or an amino protecting group such as COCH$_3$ or t-butoxycarbonyl; and
  n is an integer from 1 to about 50.

The preparation of this group of PNA oligomers is described in U.S. Pat. No. 5,719,262, issued Feb. 17, 1998, hereby incorporated by reference in its entirety.

Further PNA backbone sustitutions at the glycinyl methylene group are disclosed in U.S. Pat. No. 6,107,470, issued Aug. 22, 2000, hereby incorporated by reference in its entirety.

Further modification of the backbone including various combinations of substitution at the glycinyl methylene, varying the chain length of the aminoethyl group and or the glycinyl group, and the tethering group are amenable to the present invention. Included in this group of PNA oligomers are those having the formula:

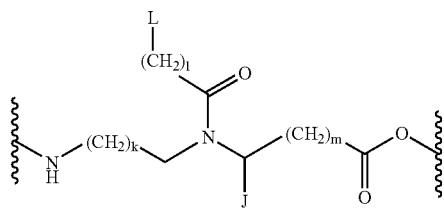

wherein each J is, independently, hydrogen or a side chain of a naturally occurring alpha amino acid;

k, m and l are each, independently, 0 or an interger from 1 to about 5; and

L is a heterocyclic base moiety.

The preparation of PNA compounds having these modifications are disclosed in U.S. Pat. No. 5,641,625, issued Jun. 24, 1997, hereby incorporated by reference in its entirety.

Further backbone modifications and substitutions are disclosed in U.S. Pat. No. 5,773,571, issued Jun. 30, 1998, hereby incorporated by reference in its entirety.

The preparation of PNA monomers and oligomers having a cyclic structure incorporated into the backbone wherein the cyclic structure could give chirality to two of the carbon atoms of the backbone is disclosed in U.S. Pat. No. 5,977,296, issued Nov. 2, 1999, and U.S. Pat. No. 6,201,103, issued Mar. 13, 2001, hereby incorporated by reference in their entirety.

Figure 2:
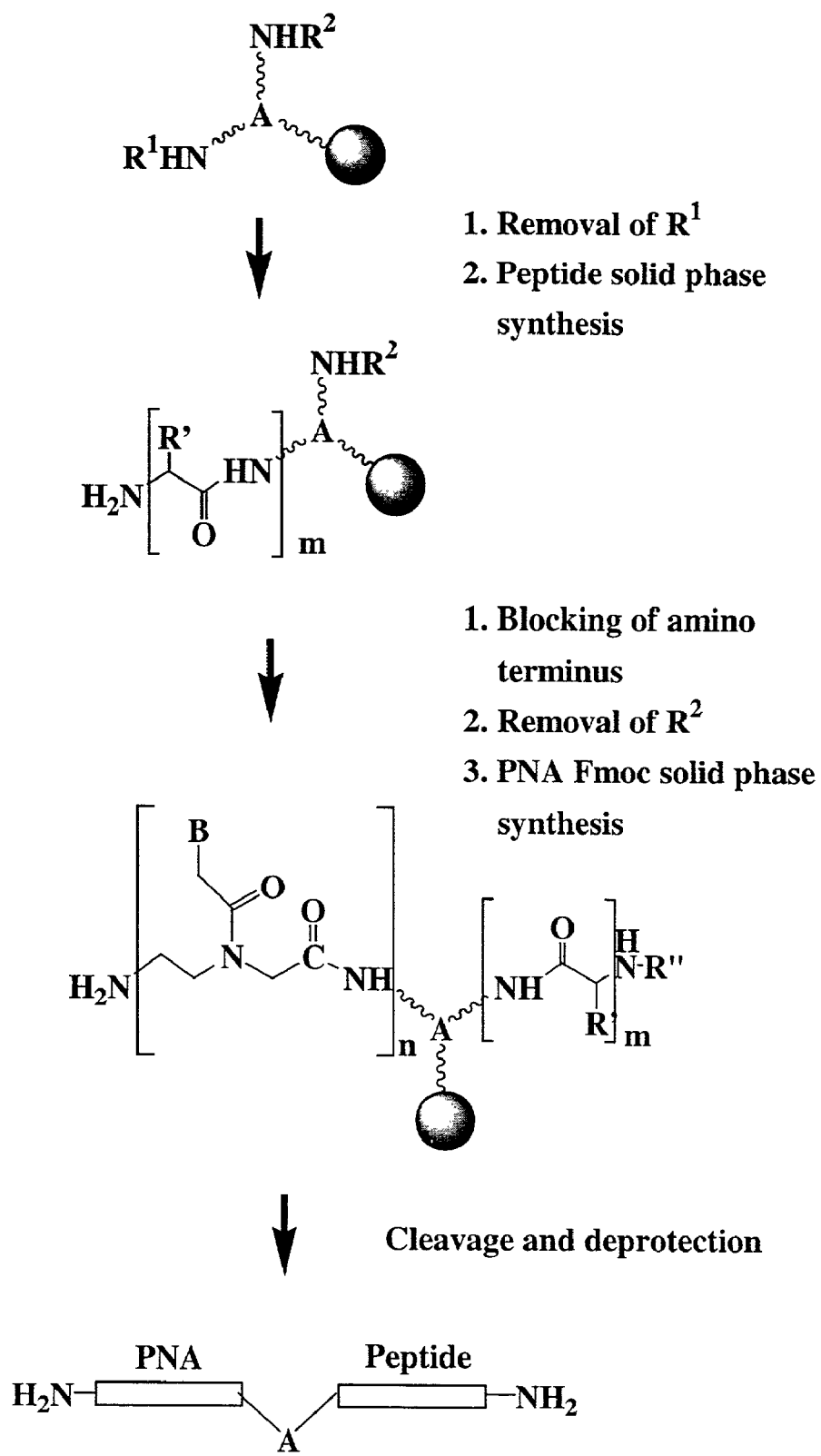
FIG. 2 is a schematic drawing of the solid phase synthesis of a PNA-peptide conjugate of the invention, wherein the peptide is synthesized first.

The synthesis of a PNA-peptide conjugate of the invention is schematically shown in FIG. 1, where the PNA is synthesized first, and in FIG. 2, where the peptide is synthesized first. Unlike "normal" peptide synthesis, stepwise chain building of achiral PNA oligomers, such as those based on aminoethylglycyl backbone units, can start either from the N-terminus or the C-terminus, because the coupling reactions are free of racemization. Those skilled in the art will recognize that whereas syntheses commencing at the C-terminus typically employ protected amine groups and free or activated acid groups, syntheses commencing at the N-terminus typically employ protected acid groups and free or activated amine groups.

Following coupling of the first amino acid, the next stage of solid-phase synthesis is the systematic elaboration of the desired PNA chain. This elaboration involves repeated deprotection/coupling cycles. The temporary protecting group, such as a Boc or Fmoc group, on the last-coupled amino acid is quantitatively removed by a suitable treatment, for example, by acidolysis, such as with trifluoroacetic acid, in the case of Boc, or by base treatment, such as with piperidine, in the case of Fmoc, so as to liberate the N-terminal amine function.

The next desired N-protected amino acid is then coupled to the N-terminal of the last-coupled amino acid. This coupling of the C-terminal of an amino acid with the N-terminal of the last-coupled amino acid can be achieved in several ways. For example, it can be bound by providing the incoming amino acid in a form with the carboxyl group activated by any of several methods, including the initial formation of an active ester derivative such as a 2,4,5-trichlorophenyl ester (Pless, et al., *Helv. Chim. Acta,* 1963, 46, 1609), a phthalimido ester (Nefkens, et al., *J. Am. Chem. Soc.,* 1961, 83, 1263), a pentachlorophenyl ester (Kuprysze-wski, *Rocz. Chem.,* 1961, 35, 595), a pentafluorophenyl ester (Kovacs, et al., *J. Am. Chem. Soc.,* 1963, 85, 183), an o-nitrophenyl ester (Bodanzsky, *Nature,* 1955, 175, 685), an imidazole ester (Li, et al., *J. Am. Chem. Soc.,* 1970, 92, 7608), and a 3-hydroxy-4-oxo-3,4-dihydroquinazoline (Dhbt-OH) ester (Konig, et al., *Chem. Bet,* 1973, 103, 2024 and 2034), or the initial formation of an anhydride such as a symmetrical anhydride (Wieland, et al., *Angew. Chem., Int. Ed. Engl.,* 1971, 10, 336). Alternatively, the carboxyl group of the incoming amino acid can be reacted directly with the N-terminal of the last-coupled amino acid with the assistance of a condensation reagent such as, for example, dicyclohexylcarbodiimide (Sheehan, et al., *J. Am. Chem. Soc.,* 1955, 77, 1067) or derivatives thereof. Benzotriazolyl N-oxy-trisdimethylamino phosphonium hexafluorophosphate (BOP), "Castro's reagent" (see, e.g., Rivaille, et al., *Tetrahedron,* 1980, 36, 3413) is recommended when assembling PNA molecules containing secondary amino groups. Finally, activated PNA monomers analogous to amino acid fluorides (Carpino, *J. Am. Chem. Soc.,* 1990, 112, 9651) hold considerable promise to be used in PNA synthesis as well.

Synthesis of Oligonucleotide Entity

Figure 3:
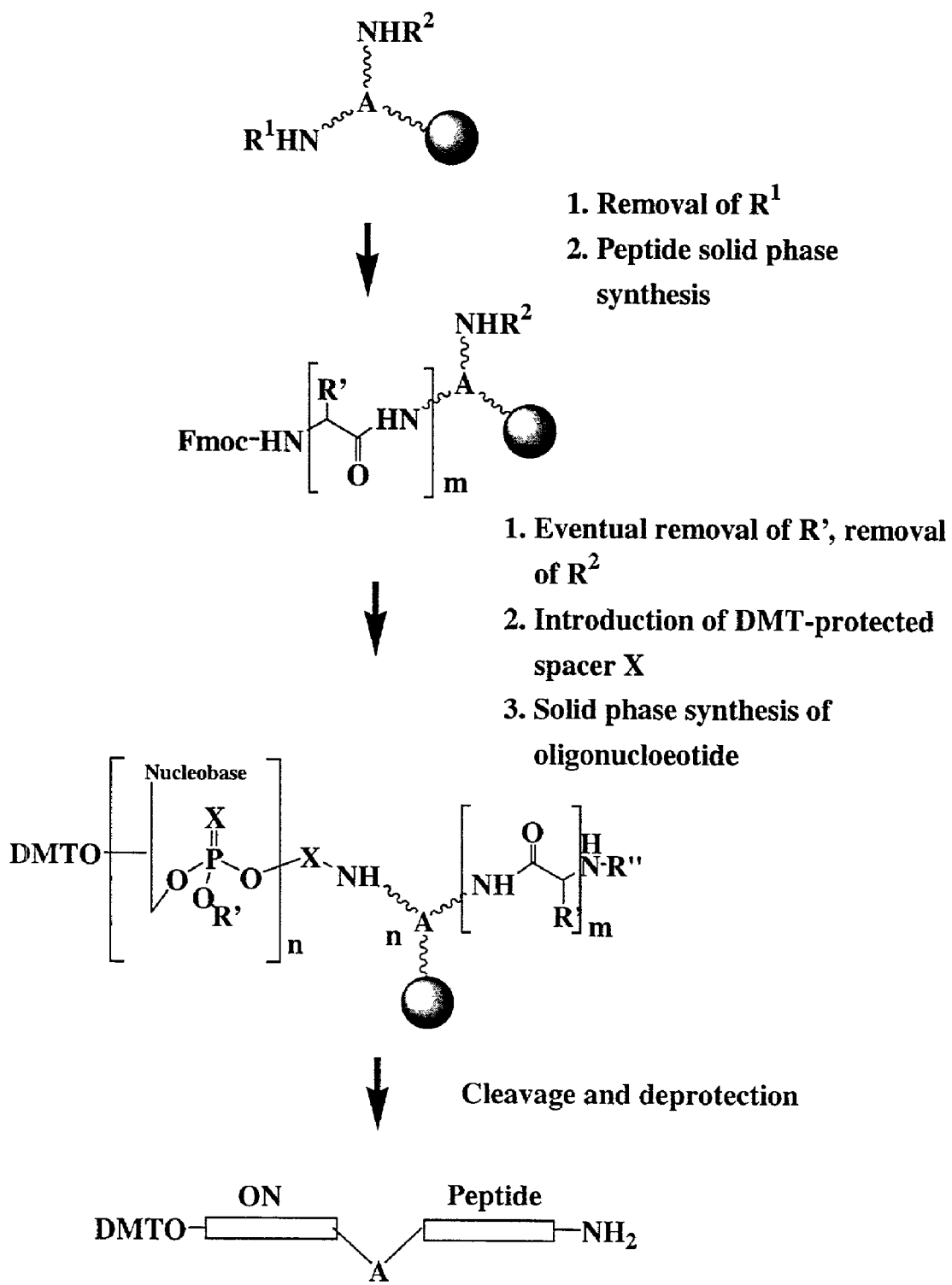
FIG. 3 is a schematic drawing of the solid phase synthesis of an oligonucleotide-peptide conjugate of the invention.

Conventional iterative solid phase oligonucleotide synthetic regimes are utilized to synthesize the oligonucleotide entities in the conjugated oligomeric compounds of the invention. Representative solid phase techniques are those typically employed for DNA and RNA synthesis utilizing standard phosphoramidite chemistry, (see, e.g., *Protocols For Oligonucleotides And Analogs,* Agrawal, S., ed., Humana Press, Totowa, N.J., 1993, hereby incorporated by reference in its entirety). Further details of methods useful for preparing oligonucleotides may be found in Sekine, M., etc al., *J. Org. Chem.,* 1979, 44, 2325; Dahl, O., *Sulfur Reports,* 1991, 11, 167–192; Kresse, J., et. al., Nucleic Acids Research, 1975, 2, 1–9; Eckstein, F., *Ann. Rev. Biochem.,* 1985, 54, 367–402; and U.S. Pat. No. 5,210,264. The synthesis of a oligonucleotide-peptide conjugate of the invention is schematically shown in FIG. 3.

The synthesis of the oligonucleotide entity of the conjugate requires first deprotecting the amino group on which the oligonucleotide will be synthesized and then introducing a protected spacer unit on the deprotected amino group. Once the protected spacer unit has been introduced, the synthesis of the oligonucleotide may be synthesized by standard phosphoamidite chemistry. See, for example, *Oligonucleotides And Analogues: A Practical Approach,* Ekstein, F. Ed., IRL Press, N.Y, 1991, hereby incorporated by reference in its entirety. The support-bound protected spacer unit attached to one of the arms of the bridging unit is then treated to remove the 5'-protecting group, typically by treatment with acid, and then is reacted with a nucleoside phosphoramidite under anhydrous conditions in the presence of an activating agent such as, for example, 1H-tetrazole, 5-(4-nitrophenyl)-1H-tetrazole, or diisopropylamino tetrazolide to form a phosphite triester linkage.

Suitable spacer units include y-butyric acid and compounds 2–6. The spacer unit must be temporarily protected. The synthesis of four suitable spacer units may proceed by the following synthesis schemes.

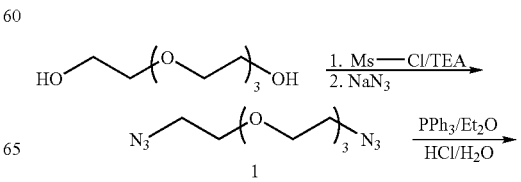

-continued

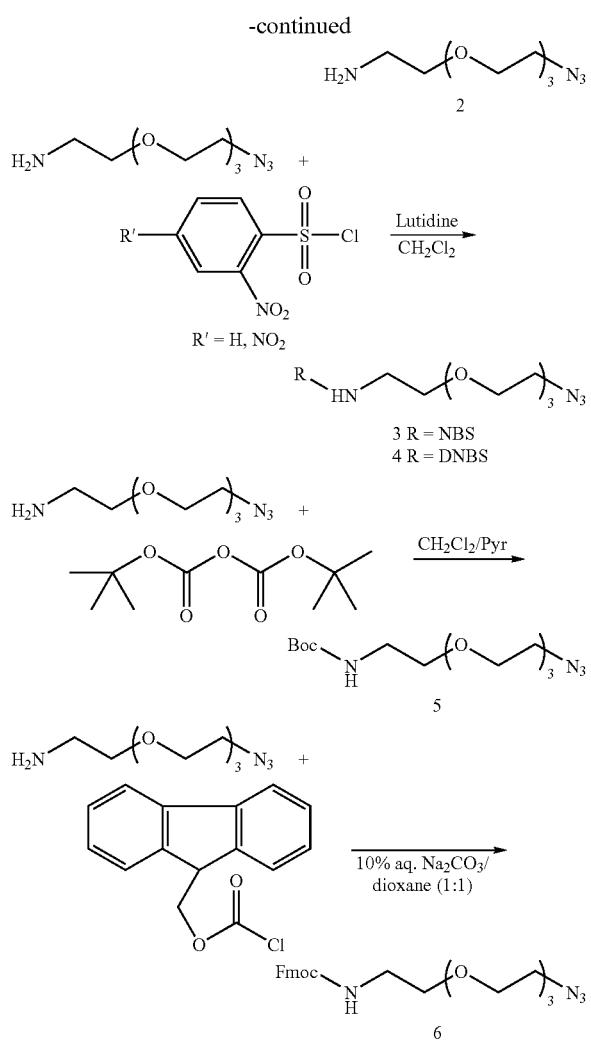

The preferred temporary protection is alkylation with 4',4'-dimethoxytritylchloride (DMT).

A preferred synthetic solid phase synthesis of oligonucleotides utilizes phosphoramidites as activated phosphate compounds. In this technique, a phosphoramidite monomer is reacted with a free hydroxyl on the growing oligomer chain to produce an intermediate phosphite compound, which is subsequently oxidized to the P$^v$ state using standard methods. This technique is commonly used for the synthesis of several types of linkages including phosphodiester, phosphorothioate, and phosphorodithioate linkages.

The phosphite triester linkage is subsequently oxidized or sulfurized. Choice of oxidizing or sulfurizing agent will determine whether the linkage will be oxidized or sulfurized to a phosphotriester, thiophosphotriester, or a dithiophosphotriester linkage.

It is generally preferable to perform a capping step, either prior to or after oxidation or sulfurization of the phosphite triester, thiophosphite triester, or dithiophosphite triester. Such a capping step is generally known to be beneficial by preventing shortened oligomer chains, by blocking chains that have not reacted in the coupling cycle. One representative reagent used for capping is acetic anhydride. Other suitable capping reagents and methodologies can be found in U.S. Pat. No. 4,816,571, hereby incorporated by reference in its entirety. Treatment with an acid removes the 5'-hydroxyl protecting group, and the synthetic cycle is repeated until the desired oligomer is achieved.

The internucleoside linkages of the oligonucleotides described herein, can be any internucleoside linkage as is known in the art, including phosphorus based linking groups such as phosphite, phosphodiester, phosphorothioate, and phosphorodithioate linkages. Such linkages can be protected, i.e., they can bear, for example, phosphorus-protecting groups. As used herein, the term "phosphorus protecting group" is intended to denote protecting groups that are known to be useful to protect phosphorus-containing linkages during oligonucleotide synthesis. One such preferred phosphorus-protecting group is the α-cyanoethyl protecting group.

Other representative phosphorus protecting groups include —CH$_2$CH=CHCH$_2$CN, para-C$_6$H$_4$CH$_2$CN, —(CH$_2$)$_{2-5}$-N(H)COCF$_3$, —CH$_2$CH$_2$Si(C$_6$H$_5$)$_2$CH$_2$, —CH$_2$CH$_2$N(CH$_3$)COCF$_3$ and others known in the art.

Representative nucleobases useful in the methods and conjugated oligomeric compounds of the invention include adenine, guanine, cytosine, uridine, and thymine, as well as other non-naturally occurring and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and cytosines, 7-methylguanine. Further naturally and non naturally occurring nucleobases include those disclosed in U.S. Pat. No. 3,687,808, in Chapter 15 by Sanghvi, in *Antisense Research and Application*, Ed. S. T. Crooke and B. Lebleu, CRC Press, 1993, in Englisch et al., *Angewandte Chemie, International Edition*, 1991, 30, 613–722 (see especially pages 622 and 623, and in the *Concise Encyclopedia of Polymer Science and Engineering*, J. I. Kroschwitz Ed., John Wiley & Sons, 1990, pages 858–859, Cook, P. D., *Anti-Cancer Drug Design,* 1991, 6, 585–607, each of which are hereby incorporated by reference in their entirety. The term "nucleosidic base" is further intended to include heterocyclic compounds that can serve as like nucleosidic bases including certain "universal bases" that are not nucleosidic bases in the most classical sense but serve as nucleosidic bases. Especially mentioned as a universal base is 3-nitropyrrole.

Representative 2'-sugar modifications amenable to the present invention include fluoro, O-alkyl, O-alkylamino, O-alkylalkoxy, protected O-alkylamino, O-alkylaminoalkyl, O-alkyl imidazole, and polyethers of the formula (O-alkyl)$_m$, where m is 1 to about 10. Preferred among these polyethers are linear and cyclic polyethylene glycols (PEGs), and (PEG)-containing groups, such as crown ethers and those which are disclosed by Ouchi, et al., *Drug Design and Discovery,* 1992, 9, 93, Ravasio, et al., *J. Org. Chem.* 1991, 56, 4329, and Delgardo et. al., *Critical Reviews in Therapeutic Drug Carrier Systems* 1992, 9, 249, each of which are hereby incorporated by reference in their entirety. Further sugar modifications are disclosed in Cook, P. D., supra. Fluoro, O-alkyl, O-alkylamino, O-alkyl imidazole, O-alkylaminoalkyl, and alkyl amino substitution is described in U.S. Pat. No. 6,166,197, hereby incorporated by reference in its entirety.

Sugars having O-substitutions on the ribosyl ring are also amenable to the present invention. Representative substitutions for ring 0 include S, CH$_2$, CHF, and CF$_2$, see, e.g., Secrist, et al., Abstract 21, Program & Abstracts, Tenth International Roundtable, *Nucleosides, Nucleotides and their Biological Applications*, Park City, Utah, Sep. 16–20, 1992, hereby incorporated by reference in its entirety.

Representative hydroxyl protecting groups commonly used in the art may be found in Beaucage, et al., *Tetrahedron* 1992, 48, 2223; and Greene and Wuts, *Protective Groups in Organic Synthesis*, Chapter 2, 2d ed, John Wiley & Sons, New York, 1991, each of which are hereby incorporated by reference in their entirety. Preferred protecting groups include dimethoxytrityl (DMT), monomethoxytrityl, 9-phenylxanthen-9-yl (Pixyl) and 9-(p-methoxyphenyl)xanthen-9-yl (Mox). The protecting group can be removed from oligonucleotides of the conjugated oligomeric compound of the invention by techniques well known in the art to form the free hydroxyl. For example, dimethoxytrityl protecting groups can be removed by protic acids such as formic acid, dichloroacetic acid, trichloroacetic acid, p-toluene sulphonic acid or with Lewis acids such as for example zinc bromide. See, for example, Greene and Wuts, supra.

In some preferred embodiments of the invention amino groups are appended to alkyl or to other groups such as, for example, to 2'-alkoxy groups. Such amino groups are also commonly present in naturally occurring and non-naturally occurring nucleobases. It is generally preferred that these amino groups be in protected form during the synthesis of oligonucleotides of the invention. Representative amino protecting groups suitable for these purposes are discussed in Greene and Wuts, *Protective Groups in Organic Synthesis*, Chapter 7, 2d ed, John Wiley & Sons, New York, 1991. Generally, as used herein, the term "protected" when used in connection with a molecular moiety such as "nucleobase" indicates that the molecular moiety contains one or more functionalities protected by protecting groups.

Deprotection and Cleavage of Conjugated Oligomeric Compound

Following assembly of the desired conjugated oligomeric compound, the next step will normally be deprotection of the amino acid and/or acid of the conjugated oligomeric compound and cleavage of the synthesized conjugated oligomeric compound from the solid support. These processes can take place substantially simultaneously, thereby providing the free conjugated oligomeric compound in the desired form.

In the above-mentioned "Boc-benzyl" protection scheme, the final deprotection of side-chains and release of the conjugated oligomeric compound from the solid support is most often carried out by the use of strong acids, such as anhydrous hydrofluoric acid (Sakakibara, et al., *Bull. Chem. Soc. Jpn.*, 1965, 38, 4921), boron tris (trifluoroacetate) (Pless, et al., *Helv. Chim. Acta*, 1973, 46, 1609), and sulfonic acids, such as trifluoromethanesulfonic acid and methanesulfonic acid (Yajima, et al., *J. Chem. Soc., Chem. Comm.*, 1974, 107). This conventional strong acid (e.g., anhydrous HF) deprotection method, produces very reactive carbocations that may lead to alkylation and acylation of sensitive residues in the peptide and PNA oligomers. Such side-reactions are only partly avoided by the presence of scavengers such as anisole, phenol, dimethyl sulfide, and mercaptoethanol and, therefore, the sulfide-assisted acidolytic $S_{N2}$ deprotection method (Tam, et al., *J. Am. Chem. Soc.*, 1983, 105, 6442 and *J. Am. Chem. Soc.*, 1986, 108, 5242), the so-called "low", which removes the precursors of harmful carbocations to form inert sulfonium salts, is frequently employed in peptide and PNA synthesis, either solely or in combination with "high" methods. Less frequently, in special cases, other methods used for deprotection and/or final cleavage of the conjugate-solid support bond are, for example, such methods as base-catalyzed alcoholysis (Barton, et al., *J. Am. Chem. Soc.*, 1973, 95, 4501), and ammonolysis as well as hydrazinolysis (Bodanszky, et al., *Chem. Ind.*, 1964 1423), hydrogenolysis (Jones, *Tetrahedron Lett.* 1977, 2853 and Schlatter, et al., *Tetrahedron Lett.* 1977 2861), and photolysis (Rich and Gurwara, *J. Am. Chem. Soc.*, 1975, 97, 1575).

In Table 1 and 2, a number of possible combinations of $R^1$ and $R^2$ and the linking unit A to the resin are listed for the synthesis of peptide conjugated oligomeric compounds without the intent to restrict or limit our invention to those combinations.

The synthesis conditions are determined by the combination of amino group protecting groups and the linking unit used to attach the bridging unit to the resin. Table 1 summarizes the various combinations and their deprotection and cleavage conditions. The solid phase syntheses, purification and analysis of the conjugated oligomeric compounds may be performed as described under General Procedures and in Examples 16 and 17.

TABLE 1

| Unit | $R^1$ | Cleavage Conditions | $R^2$ | Cleavage conditions | Linking unit A | Cleavage/deprotection conditions |
|---|---|---|---|---|---|---|
| 13 | Fmoc | 20% Pip in DMF | NBS | Thiol/TEA | PAL, XAL, Tr HMBA | TFA TFA → base |
| 12 | Fmoc | 20% Pip in DMF | —N=N=N | PMe₃/THF/H₂O | PAL, XAL, Tr HMBA | TFA TFA → base |
| 9, 10 | DNBS, NBS | Thiol/TEA | —N=N=N | PMe₃/THF/H₂O | PAL, XAL, Tr HMBA | TFA TFA → base |
| 14 | Boc | TFA/mCresol (95:5) | Fmoc | 20% Pip in DMF | MBHA | TFMSA |
| 11 | Boc | TFA/mCresol (95:5) | —N=N=N | PMe₃/THF/H₂O | MBHA | TFMSA |

The first three combinations allow two consecutive syntheses (PNA followed by peptide synthesis or vice versa) with Fmoc chemistry. Therefore, a moderately acid-labile linking unit to the resin can be used and the conjugated oligomeric compound is cleaved and deprotected by TFA. This creates a high versatility with respect to the nature of the conjugated oligomeric compounds, which can be synthesized by this method. The last two combinations use the Boc strategy for synthesizing the first entity followed by Fmoc for the synthesis of the second entity. Regardless of the linking unit used for this combination, this approach generally involves the deprotection of the bases (or amino acid side chains) with at least low TFMSA before or after cleavage from the resin. This limits the application of this approach to conjugated oligomeric compounds of sufficient stability to strong acids like TFMSA.

Table 2 shows the combinations of amino protecting groups and linking units that can be used for solid phase synthesis of oligonucleotide-peptide conjugates:

TABLE 2

| Unit | R¹ | Cleavage Conditions | R² | Cleavage conditions | Linking unit A | Cleavage/ deprotection conditions |
|---|---|---|---|---|---|---|
| 12 | Fmoc | 20% Pip in DMF | —N=N=N | PMe₃/THF/H₂O | HMBA | Base |
| 13 | Fmoc | 20% Pip in DMF | NBS | Thiol/TEA | HMBA | Base |
| 9, 10 | DNBS | Thiol/TEA | —N=N=N | PMe₃/THF/H₂O | HMBA | Base |
| 14 | Boc | TFA/mCresol (95:5) | Fmoc | 20% Pip in DMF | HMBA | Base |
| 11 | Boc | TFA/mCresol (95:5) | —N=N=N | PMe₃/THF/H₂O | HMBA | Base |

Commercially available amino acids suitable for the synthesis of oligonucleotide-peptide conjugates include Boc-Ala-OH, Boc-Cys(Acm)-OH, Boc-Gly-OH, Boc-Glu(t-Bu)-OH, Boc-Asp(t-Bu)-OH, Boc-His(Boc)-OH, Boc-Ile-OH, Boc-Leu-OH, BocLys(Fmoc)-OH, Boc-Met-OH, Boc-Orn (Fmoc)-OH→Arg by postsynthetic guanidinylation, Boc-Phe-OH, Boc-Pro-OH, Boc-Ser(t-Bu)-OH, Boc-Thr(t-Bu)-OH, Boc-Trp(For)-OH, Boc-Tyr(t-Bu)-OH, Boc-Val-OH.

Preferred Methods of Use

In a preferred embodiment, the conjugated oligomeric compound of the invention may be administered in an effective amount to an organism to inhibit expression of a gene in the organism. Those skilled in the art would readily be able to determine the effective amount of the conjugated oligomeric compound based on the characteristics of the gene.

In another preferred embodiment, the conjugated oligomeric compound of the invention may be contacted in an effective amount to kill a pathogenic organism. Those skilled in the art would readily be able to determine the effective amount of conjugated oligomeric compound to kill the organism.

In yet another preferred embodiment, the conjugated oligomeric compound of the invention may be used to improve the intracellular delivery of PNAs or oligonucleotides to an organism.

The conjugated oligomeric compounds of the invention may be used in the therapeutic and/or prophylactic treatment of unicellular prokaryotic and multicellular eukaryotic organisms that utilize DNA-RNA transcription or RNA-protein transcription as a fundamental part of its hereditary, metabolic or cellular control. Such treatment may include the use of the conjugated oligomeric compounds of the invention in a method for killing a pathogenic organism, including viruses, bacteria and eukaryotic parasites.

For therapeutic or prophylactic treatment, the conjugated oligomeric compounds of the invention may be formulated in a pharmaceutical composition, which may include carriers, thickeners, diluents, buffers, preservatives, surface active agents and the like. Pharmaceutical compositions may also include one or more active ingredients such as antimicrobial agents, antiinflammatory agents, anesthetics, and the like in addition to the conjugated oligomeric compound of the invention A pharmaceutical composition containing the conjugated oligomeric compounds of the invention may be administered in a number of ways depending on whether local or systemic treatment is desired, and on the area to be treated. Administration may be performed topically (including ophthalmically, vaginally, rectally, transdermally, intranasally), orally, by inhalation, or parenterally, for example by intravenous infusion, drip or injection, or subcutaneous, intraperitoneal or intramuscular injection.

In addition, the conjugated oligomeric compounds of the invention may be used for diagnostic and research purposes, as will be apparent to those skilled in the art.

Compounds of the present invention are preferably specifically hydridizable with a target region. By "specifically hybridizable" herein is meant capable of forming a stable duplex with a target DNA or RNA. It is believed that oligonucleotides which form Watson-Crick base pairs, i.e. are complementary with target DNA or RNA and which specifically hybridize with target DNA or RNA inhibit the flow of genetic information from DNA to protein. In some embodiments of the present invention the oligonucleotide portions of compounds of the present invention are at least 70% complementary to a target sequence. In preferred embodiments of the present invention the oligonucleotide portions of compounds of the present invention are at least 80% complementary to a target sequence. 100% complementarity of the oligonucleotide portions of compounds of the present invention to a target sequence is most preferred. In preferred embodiments of the present invention, the oligonucleotide portions may be specifically hybridizable with DNA or RNA from papilloma virus, herpes viruses, human immunodeficiency virus, *Candida*, cytomegaloviruses, and influenza viruses. In addition, the oligonucleotide portions may also be specifically hybridizable with endogenous DNA or RNA of a cell.

For therapeutics, an animal suspected of having a disease characterized by excessive or abnormal production of a protein is treated by administering the conjugated oligomeric compounds of the invention in a pharmaceutically acceptable carrier. Most preferable, the compound is hybridizable with an RNA coding for the protein. Persons of ordinary skill in the art can easily determine optimum dosages, dosing methodologies and repetition rates. Such treatment is generally continued until either a cure is effected or a diminution in the diseased state is achieved. Long term treatment is likely for some diseases.

The compounds of the present invention will also be useful as a research reagent useful for the modulation of the production of a protein by an organism. Modulation may be accomplished by contacting the organism with the conjugated oligomeric compounds of the invention. Preferably the compounds are hybridizable with RNA coding for the protein.

Diagnostic applications include the detection of the presence or absence of an RNA in a sample suspected of containing RNA comprising contacting the sample with a conjugated oligomeric compound of the present invention wherein the conjugated oligomeric compound is specifically hybridizable with the RNA and detecting the presence or absence of hybridization of the compound to the sample wherein hybridization is indicative of the present of the RNA in the sample.

The following examples are illustrative but are not meant to be limiting of the present invention.

EXAMPLES

General Procedures

Abbreviations

Bhoc, benzhydryloxycarbonyl; Boc, t-butyloxycarbonyl; t-Bu, tert.-butyl; Cbz, benzyloxycarbonyl; DCM, dichloromethane; DIEA, N,N-diisopropylamine; DMF, dimethylformamide; DMS, dimethylsulfide; DNBS, 2,4-dinitrobenzenesulfonyl; ESI-MS, electrospray ionization mass spectrometry; Fmoc, 9-fluorenylmethoxycarbonyl; HATU, O-(7-azabenzotriazol-1-yl)-1,1,3,3-tetramethyluronium hexafluorophosphate; HBTU, 2(1H-benzotriazole-1-yl)-1,1,3,3 tetramethyluronium hexafluorophosphate; HMBA, 4-hydroxymethylbenzoic acid; HOBt, N-hydroxybenzotriazole; 2'-O-MOE, 2'-O-methoxyethyl; MBHA, p-methylbenzhydrylamine; NBS, 2 and 4-nitrobenzenesulfonyl; NMP, N-methylpyrrolidinone; PAL, 5-(4'-aminomethyl-3',5'-dimethoxyphenoxy)valeric acid; PNA, peptide nucleic acid; RP-HPLC, reversed phase high performance liquid chromatography; TEA, triethylamine; TFA, trifluoroacetic acid; TFMSA, trifluoromethanesulfonic acid; THF, tetrahydrofuran; TIS, triisoproylsilane; Ttr, trityl; XAL, 9-aminoxanthen-3-yloxy.

Reagents and Solvents

The solvents used for the preparation of the branched bridging units and solid phase synthesis of PNA and peptides were purchased from Aldrich or J. T. Baker in the highest grade available. Amino acids including Boc-protected γ-aminobutyric acid, the resins used for solid phase synthesis, HBTU and HOBt were purchased from Novabiochem. PNA monomers (Fmoc and Boc-protected) and HATU were obtained from Applied Biosystems. All other reagents were purchased from Sigma-Aldrich.

Solid Phase Synthesis of PNA Conjugated Oligomeric Compounds

The PNA entities of the conjugated oligomeric compounds were assembled on one of the amino groups of the branched bridging unit after removal of the amino protection $R^1$ by solid phase synthesis. The synthesis was carried out either manually in special fabricated glass columns or using an Applied Biosystems 433 A Peptide Synthesizer according to previously published procedures for PNA synthesis (Boc chemistry). For Fmoc chemistry the manufacturer's protocols were adapted to the specific synthesis procedures used. The second part of the conjugated oligomeric compounds (e.g. peptides) was synthesized by solid phase synthesis on the second amino group of the branched bridging unit after removal of the amino protection $R^2$. Deprotection and cleavage conditions for the conjugated oligomeric compounds were determined by the protecting groups of exocyclic amino groups of the nucleobases and the linking unit used for the attachment of the branched unit to the resin:

For Cbz-protection and MBHA linking unit combinations: one volume of a solution of TFA/DMS/mCresol (1:3:1) was mixed with one volume of TFA/TFMSA (9:1) and added to the resin. After 1 hour of shaking the resin was washed with TFA and one volume of TFA/TFMSA/mCresol (8:2:1) was added and the suspension was shaken for another 1.5 hours.

For Bhoc-protection and XAL/PAL or base labile linking unit combinations: a mixture of TFA/m-cresol/TIS/H$_2$O (94:2.5:1:2.5) was added to the resin and the suspension was shaken for 15 min. Then the resin was filtered off and the filtrate was allowed to stand for another 3–6 hours.

For both chemistries, the filtrate was then added to a 10-fold volume of cold ether, mixed and centrifuged. The supernatant was removed and the pellet was resuspended in ether. This was repeated three times. The pellet was dried and re-dissolved in water or 0.1% TFA for HPLC purification.

Solid Phase Synthesis of Oligonucleotide Conjugated Oligomeric Compound

For synthesis of oligonucleotide conjugated oligomeric compounds, generally the non-nucleotidic part (e.g. peptide) is synthesized by solid phase synthesis on the first amino group of the branched bridging unit after removal of the amino protection $R^1$. Then the oligonucleotide part of the conjugated oligomeric compound is synthesized by solid phase synthesis on the second amino group of the branched bridging unit after removal of the amino protection $R^2$. Deprotection and cleavage of the conjugated oligomeric compounds is generally performed under basic conditions, which requires a base-labile linking unit, onto which the branched bridging unit is attached to the resin and base labile side chain protection for the amino acids. After deprotection, the basic solution is evaporated and the conjugated oligomeric compound is dissolved in water for HPLC purification.

HPLC Purification of PNA Conjugated Oligomeric Compounds

The conjugated oligomeric compounds were purified by RP-HPLC using a 306 Piston Pump System, an 811C Dynamic Mixer, a 70 Diode Array Detector and a 215 Liquid Handler together with the Unipoint Software (Gilson) and Jupiter (Phenomenex) or Zorbax (Hewlett Packard), C$_{18}$, 300 Å columns. 0.1% TFA in H$_2$O (A) and CH$_3$CN (B) were used as the solvent system. The applied gradient was dependent on the length and sequence of the conjugated oligomeric compound. Dual wavelength detection was carried out at 220 and 260 nm and the column temperature was kept between room temperature and 60° C. depending on the tendency of the conjugated oligomeric compounds for secondary structure formation.

HPLC Purfication of Oligonucleotide Conjugated Oligomeric Compounds

The conjugated oligomeric compounds were purified by RP-HPLC using a 306 Piston Pump System, an 811C Dynamic Mixer, a 70 Diode Array Detector and a 215 Liquid Handler together with the Unipoint Software (Gilson). The columns used and the applied solvent system and gradient is dependent on the length and sequence of the conjugated oligomeric compound. Dual wavelength detection is carried out at 220 and 260 nm.

Example 1

Synthesis of 1,11-Diazido-3,6,9-trioxaundecane (1)

50.78 g (0.2614 mol) of tetraethylene glycol were dried by coevaporation with toluene (3×100 mL) and 200 mL of THF were added. 45 mL (0.5814 mol) mesyl chloride were added to the stirred mixture under argon atmosphere and the mixture was cooled on an ice bath before 81 mL (0.5811 mol) of TEA in 50 mL THF were added dropwise over a period of 30 minutes under stirring. After 1 hour, the ice bath was removed and the mixture was stirred for another 3.5 hours at room temperature. After the addition of water (130 mL) the precipitate dissolved and two liquid phases were formed, which were chilled on an ice bath before 12 g of $NaHCO_3$ were added. After evaporation of most of the TBF, 34.88 g (0.5365 mol) of $NaN_3$ were added and the mixture was refluxed under stirring at 86° C. for another 24 hours. Some water was added during the reflux process to completely dissolve the $NaN_3$. After the mixture was cooled down to room temperature, the product was extracted with 100 mL portions of diethyl ether (5×) and the ether layers were backwashed with the same 50 mL portion of saturated aqueous $NaHCO_3$. The ether layers were combined, dried over $Na_2SO_4$, filtered and concentrated by rotary evaporation. The product was obtained as an amber oil after traces of solvent were removed under high vacuo (55 g≅86% of theoretical yield). $^1$H-NMR ($CDCl_3$): δ 3.68 (m, 12H), δ 3.39 (t, J=5.2 Hz, 4H).

Example 2

Synthesis of 1-Amino-11-azido-3,6,9-trioxaundecane (2)

52 g (0.212 mol) of 1,11-diazido-3,6,9-trioxaundecane (1) were stirred with 480 ml of 5% aqueous HCl and a solution of 47.8 g (0.182 mol) PPh3 in 350 ml diethyl ether was added dropwise under stirring during a period of 45 minutes. After stirring for another 24 hours, the precipitate was filtered off and the separated aqueous layer was washed 3× with 100 mL portions of diethyl ether. Then, 41.4 g KOH were added to the aqueous layer (to pH 11) and the solution was allowed to stand at 4° C. for 16 hours. Any further precipitate was filtered off and the mixture was further basified by adding another 93 g of KOH. The product formed a second layer and was extracted 7× with 100 mL portions of DCM. The combined organic phases were dried over $Na_2SO_4$, filtered and concentrated by rotary evaporation to yield an amber oil, which was used without any further purification (35.7 g≅77% of theoretical yield). $^1$H-NMR ($CDCl_3$): δ 3.68 (m, 10H), δ 3.54 (t, J=5 Hz, 2H), δ 3.39 (t, J=5 Hz, 2H), δ 2.86 (t, J=5 Hz, 2H), δ 1.49 (br, s, 2H). See Schwabacher, A. W. et al. (1998) *J. Org. Chem.* 63, 1727–1729.

Example 3

Synthesis of 1-(N-2-nitrobenzenesulfonyl)-1-amino-11-azido 3,6,9-trioxaundecane (3)

4.77 g (0.0219 mol) 1-amino-11-azido-3,6,9-trioxaundecane (2) were dissolved in DCM and 3.07 mL (0.0263 mol) lutidine were added. A solution of 5.08 g (0.0229 mol) 2-nitrobenzenesulfonyl chloride in 80 mL DCM were added within 5 minutes under stirring and argon atmosphere. After all the starting material were consumed, the mixture was poured into 200 mL of saturated aqueous $NaHCO_3$. The organic phase was separated, washed 7×with 100 mL portions of saturated aqueous $NaHCO_3$ and brine and dried over $Na_2SO_4$. The oil, which was obtained after evaporation of the solvent, was used without any further purification.

Example 4

Synthesis of 1-(N-2,4-dinitrobenzenesulfonyl)-1-amino-11-azido 3,6,9-trioxaundecane (4)

4.77 g (0.0219 mol) 1-amino-11-azido-3,6,9-trioxaundecane (2) were dissolved in DCM and 3.07 mL (0.0263 mol) lutidine were added. A solution of 6.13 g (0.0229 mol) 2,4-dinitrobenzenesulfonyl chloride in 80 mL DCM were added within 5 min under stirring and argon atmosphere. After all the starting material was consumed, the mixture was poured into 200 mL of saturated aqueous $NaHCO_3$. The organic phase was separated, washed 7×with 100 mL portions of saturated aqueous $NaHCO_3$ and brine and dried over $Na_2SO_4$. After evaporation of the solvent, a dark red-brown oil was obtained, which was used without any further purification (9.2 g≅94% of theoretical yield). $^1$H-NMR ($CDCl_3$): δ 8.69–8.34 (m, 3H), δ 6.2 (br, s, 1H), δ 3.66–3.51 (m, 12H), δ 3.36 (m, 4H).

Example 5

Synthesis of 1-(N-t-butyloxycarbonyl)-1-amino-11-azido-3.6,9-tioxaundecane (5)

7.16 g (0.0328 mol) 1-amino-11-azido-3,6,9-trioxaundecane (2) were dissolved in DCM/pyridine (3:1) and a solution of 7.16 g (0.0328 mol) Boc2O in 60 mL DCM was added under stirring and argon atmosphere within 5 min. After 30 min of stirring, the reaction mixture was poured into 200 mL of saturated aqueous $NaHCO_3$, washed 3×with 50 mL portions of saturated aqueous $NaHCO_3$ and brine and dried over $Na_2SO_4$. After evaporation of the solvent, the product was obtained as an amber oil, which was used without any further purification (9.5 g≅91% of theoretical yield). $^1$H-NMR ($CDCl_3$): δ 3.67 (m, 10H), δ 3.55 (t, J=5.2 Hz, 2H), δ 3.35 (m, 4H), δ 1.45 (s, 9H).

Example 6

Synthesis of 1-(N-fluorenylmethoxycarbonyl)-1-amino-11-azido-3,6,9-trioxaundecane (6)

To a solution of 1-amino-11-azido-3,6,9-trioxaundecane (2) in dioxane/aqueous 5% $Na_2CO_3$ (1:1) containing 1 equiv. DIEA, 1 equiv. Fmoc-Cl in dioxane is added slowly under stirring and cooling on an ice bath. The mixture is stirred at room temperature for an additional 2 h, before the solution is extracted with ethyl acetate. The combined organic layers are dried over $Na_2SO_4$ and the solvent is evaporated. The product 6 is used without any further purification.

Example 7

Synthesis of 1-[N,N-bis (acetic acid tert, butylester)]-1-amino-11-azido-3,6,9-trioxaundecane (7)

To a stirred solution of 2.18 g (0.01 mol) of 1-amino-11-azido-3,6,9-trioxaundecane (2) in 40 mL DMF/$CH_3CN$ (1:1) 6.84 g (0.021 mol) $Cs_2CO_3$ were added. After 15 min 4.43 mL (0.03 mol) tert.-butyl bromoacetate were added under argon atmosphere with a syringe and the mixture was stirred for 48 hour at room temperature Then the reaction mixture was filtered through celite and the filtrate was evaporated in vacuo, dissolved in 100 mL ethyl acetate and washed 4×with 50 mL portions of 5% NaHCO$_3$ and once with brine. The organic phase was dried over Na$_2$SO$_4$ and evaporated. The product 7 was purified by silica gel chromatography to yield an amber oil (3.1 g≅69% of theoretical yield). $^1$H-NMR (CDCl$_3$): δ 3.66–3.59 (m, 12H), δ 3.49 (s, 4H), δ 3.39 (t, J=5 Hz, 2H), δ 2.94 (m, 2H), δ 1.46 (s, 18H).

stirred for another 12–24 hours. After the reaction was complete, an excess of DCM was added and the organic phase was extracted with water (5×) and washed with brine. The organic phase was dried over Na$_2$SO$_4$ and evaporated to yield the crude products (9–12), which were purified by silica gel chromatography.

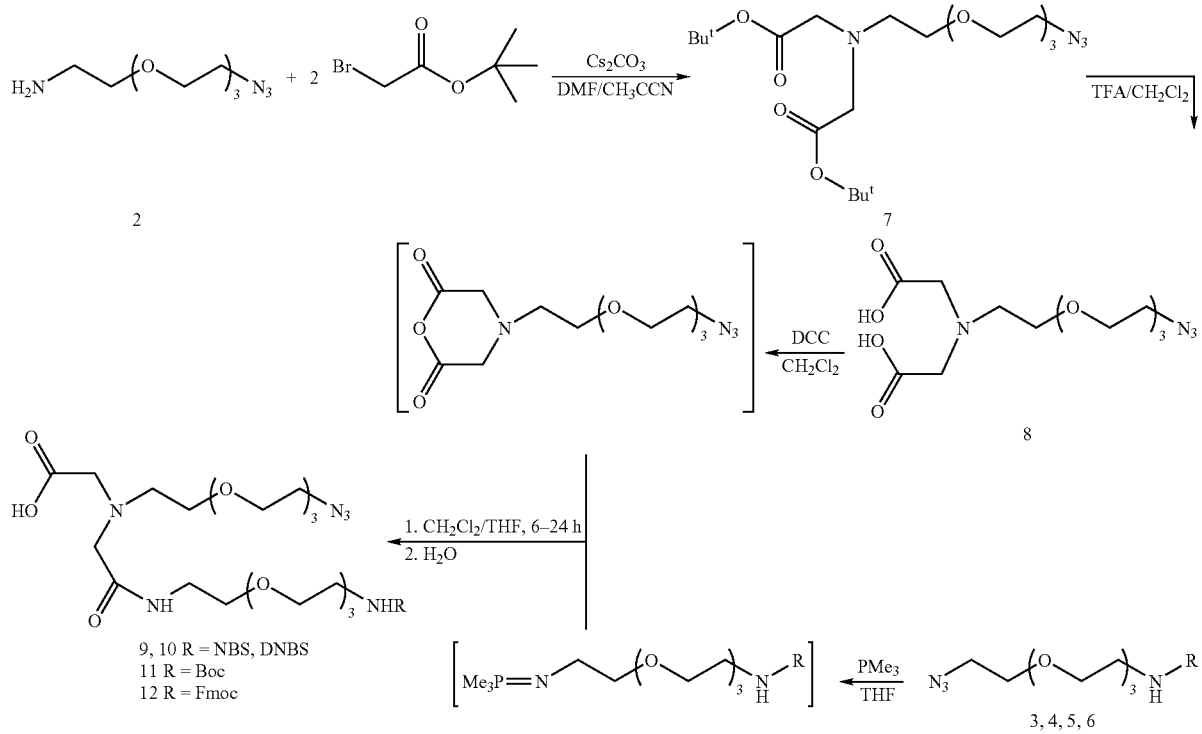

Example 8

Synthesis of 1-(N,N-diacetic acid)-1-amino-11-azido-3,6,9-trioxaundecane (8)

To a solution of 2.4 g (0.1 mol) 1-[N,N-bis (acetic acid tert. butylester)]-1-amino-11-azido-3,6,9-trioxaundecane (7) in 10 mLDCM, 10 mL (0.13 mol) TFA were added under stirring at 0° C. The solution was stirred at room temperature until the ester cleavage was complete and evaporated under vacuum. After co-evaporation with two 20 mL portions each of EtOH and toluene, the residual oil was dried under high vacuum for at least 24 hours.

Example 9

Synthesis of substituted 4-(N,N-diacetic acid)-1-amino-11-azido-3,6,9-trioxaundecane (9–12)

To a solution of 1-(N,N-diacetic acid)-1-amino-11-azido-3,6,9-trioxaundecane (8) in DCM, 1.0 equivalent of DCS was added and the solution was stirred at room temperature for 5–12 hours. Simultaneously, to a solution of 0.9 equivalents of the spacer units (3–6) in TIHF, 0.9 equivalents of PMe$_3$ (1 M solution in THF) were added under stirring and the mixture was stirred until no more azide was detected by TLC (ca. 1 hour). The two solutions were combined and

Example 10

Replacement of azido by Fmoc in substituted 4-(N, N-diacetic acid)-1-amino-11-azido-3,6,9-trioxaundecanes 9 and 11 (13, 14)

To a solution of substituted 4-(N,N-diacetic acid)-1-amino-11-azido-3,6,9-trioxaundecanes (9, 11) in dioxane/aqueous 5% Na$_2$CO$_3$ (1:1) containing 1 equivalent DIEA, 1 equivalent Fmoc-Cl in dioxane was added slowly under stirring and cooling on an ice bath. The mixture was stirred at room temperature for an additional 2 hours before the solution is extracted with ethyl acetate. The combined organic layers were dried over Na$_2$SO$_4$ and the solvent was evaporated. The compounds 13, 14 were precipitated in hexanes/diethylether.

-continued

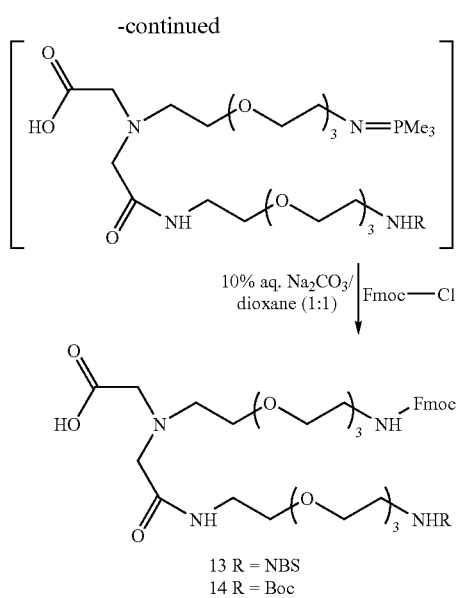

13 R = NBS
14 R = Boc

Example 11

Loading of Amino-functionalized PS Resin (Macroporous) with HMBA 1 g of the amino-functionalized macroporous PS resin was placed in a custom fabricate glass column and the resin was washed 2×with DMF. The resin was suspended in NMP and 10 equivalents of HMBA relative to the resin loading were dissolved in NMP and 10 equivalents HATU were added followed by 60 equivalents DIEA. After 3 minutes of pre-activation, the activated HMBA was added to the resin by shaking the suspension. After shaking the suspension at room temperature for another 2 hours, the resin was treated with aqueous $NH_3$ to cleave any unwanted ester linkages, washed with DMF and DCM and the loading of the resin with HMBA was confirmed qualitatively by Kaisertest. Any unreacted amino groups were capped by shaking the resin in 10 mL of $Ac_2O$/pyridine/NMP (1:2:2) for 1 hour. Completion of capping was confirmed by Kaisertest and the resin was washed with DMF followed by DCM and dried in vacuo overnight.

Example 12

Loading of MBHA PS Resin with N-α-t-Boc-ε-Fmoc-lysine 6 g of the MBHA resin were placed in a custom fabricate glass column and the resin was washed 3×with DMF and 2×with DCM, before it was allowed to swell in DCM for about 1 hours. After removal of DCM by filtration, the resin was suspended in ca. 20 mL NMP. 0.469 g (1.002 mmol) BocLys(Fmoc)OH was dissolved in NMP and 0.381 g (1.002 mmol) HATU was added followed by 1.029 mL (6.012 mmol) DIEA. After 3 minutes of pre-activation, the activated monomer was added to the resin by vigorously shaking the suspension. After shaking the suspension at room temperature for another 2 hours, the resin was washed with DMF and DCM and unreacted amino groups were capped by shaking the resin in 50 mL of $Ac_2O$/pyridine/NMP (1:2:2) for 1 hour. Completion of capping was confirmed by Kaiseitest and the resin was washed with DMF followed by DCM and dried in vacuo overnight. The loading of the resin was determined spectrophotometrically measuring the absorbance of fluorescence at 302 nm after cleaving Fmoc with 20% piperidine in DMF. Resin loading: 0.126 mmol $NH_2$/g.

Example 13

Loading of MBHA PS Resin with the Bridging Units 9–14

1 g of the MBHA resin was placed in a custom fabricate glass column and the resin was washed 3× with DMF and 2× with DCM, before it was allowed to swell in DCM for about 1 hour. After removal of DCM by filtration, the resin was suspended in NMP. 0.167 mmol of bridging units (9–14) were dissolved in NMP and 63.5 mg (0.167 mmol) HATU were added followed by 0.172 mL (1.002 mmol) DIEA. After 3 minutes of pre-activation, the activated monomer was added to the resin by vigorously shaking the suspension. After shaking the suspension at room temperature for another 2 hours, the resin was washed with DMF and DCM and unreacted amino groups were capped by shaking the resin in 10 mL of $Ac_2O$/pyridine/NMP (1:2:2) for 1 hour. Completion of capping was confirmed by Kaisertest and the resin was washed with DMF followed by DCM and dried in vacuo overnight. The loading of the resin was determined spectrophotometrically as described in Example 12. In the case of branched bridging units (9–11) an excess of FmocGly is coupled to one of the amino groups after removal of its protecting group, before the Fmoc assay was performed.

Example 14

Loading of HMBA-PEG-PS Resin with the Bridging Units (9–14)

1 g of the HMBA-PEG-PS resin was placed in a custom fabricate glass column and the resin was washed 3×with DMF and 2×with DCM, before it was allowed to swell in DCM for about 1 hours. After removal of DCM by filtration, the resin was suspended in DMF. 6 equivalents (relative to the resin loading) of the branched bridging units (9–14) were dissolved in DCM a solution of 3 equivalents DIC in DCM were added. The mixture was stirred in an ice bath for 20 minutes, then DMF was added to dissolve the formed anhydride and mixture was stirred at room temperature for another 10 minutes. The anhydride solution was added to the resin followed by a solution of 1 equivalent DMAP in DMF. After shaking the suspension at room temperature for 3–12 hours, the resin was washed with DMF and DCM and unreacted amino groups were capped by shaking the resin in 10 mL of $Ac_2O$/pyridine/NMP (1:2:2) for 1 hour. Completion of capping was confirmed by Kaisertest and the resin was washed with DMF followed by DCM and dried in vacuo overnight. The loading of the resin was determined spectrophotometrically as described in Example 12. In the case of branched bridging units (9–11) an excess of FmocGly is coupled to one of the amino groups after removal of its protecting group, before the Fmoc assay was performed.

Example 15

Loading of HMBA-PS (Macroporous) resin with the disubstituted 4-(N,N-diacetic acid) 4-aminobutanoic acid bridging units (9–14)

1 g of the HMBA-PS (macroporous) resin was placed in a custom fabricate glass column and the resin is washed 2× with DMF. The resin was suspended in DMF. 6 equivalents (relative to the resin loading) of the branched bridging units (9–14) are dissolved in DCM a solution of 3 equivalents DIC in DCM were added. The mixture was stirred in an ice bath for 20 minutes, then DMF was added to dissolve the formed anhydride and mixture was stirred at room temperature for another 10 minutes. The anhydride solution was added to the resin followed by a solution of 1 equivalent DMAP in DMF. After shaking the suspension at room temperature for 3–12 hours, the resin was washed with DMF and DCM and unreacted amino groups were capped by shaking the resin in 10 mL of $Ac_2O$/pyridine/NMP (1:2:2) for 1 hour. Completion of capping was confirmed by Kaiser test and the resin is washed with DMF followed by DCM and dried in vacuo overnight. The loading of the resin was determined spectrophotometrically as described in Example 12. In the case of branched bridging units (9–11) an excess of FmocGly was coupled to one of the amino groups after removal of its protecting group, before the Fmoc assay was performed.

Example 16

Synthesis of PNA-Peptide conjugates with N-α-t-Boc-ε-Fmoc-lysine as the bridging unit The following PNA-peptide conjugates have been synthesized using N-α-t-Boc-ε-Fmoc-lysine as a bridging unit attached to MHBA-PS resin:

pounds were cleaved, deprotected and purified as described under General Procedures. The purity and identity of the conjugated oligomeric compounds were confirmed by HPLC and ESI-MS.

Example 17

Synthesis of PNA-peptide Conjugates using Branched Bridging Units (9–14)

The synthesis conditions are determined by the combination of amino group protecting groups and the linking unit used to attach the bridging unit to the resin. Table 1 summarizes the various combinations and their deprotection and cleavage conditions. The solid phase syntheses, purification and analysis of the conjugated oligomeric compounds are performed as described under General Procedures and in Example 16.

Example 18

Synthesis of Oligonucleotide-peptide Conjugates using Branched Bridging Units (9–14)

In the case of oligonucleotide-peptide conjugates, a base-labile linking unit (e.g. HMBA) together with an appropriate choice of amino acid side chain protection groups have to be used in order to make this approach compatible with the conditions and requirements of oligonucleotide synthesis. Therefore, the peptide part of the conjugated oligomeric compound is synthesized first using Boc-chemistry, whereas the final N-terminal amino acid should either carry an N-α-Fmoc group or the N-terminus should be further modified (e.g. acetylated). During peptide synthesis acid-labile side chain protecting groups (t-Bu, Boc) are also at least partially removed, which does not interfere with the peptide synthesis. However, before oligonucleotide synthesis, the peptide on the resin is treated with TFA/m-cresol/water/TIS to completely remove the side chain protections. OH and

| Name | Sequence N→C | | $MW_{calc.}$ | $MW_{found}$ |
|---|---|---|---|---|
| SupF PNA-KFF | JJJ JJT TJJ T-O-O-O-TCC TTC CCC C-(Lys)$_3$ KFFKFFKFFK | (SEQ ID NO: 1) | 7344.9 | 7348 |
| SupF PNA-pAntp | JJJ JJT TJJ T-O-O-O-TCC TTC CCC C-(Lys)$_3$ RQIKIWFQNRRMKWKK | (SEQ ID NO: 2) | 8177.9 | 8182 |

J = pseudoisocytosine PNA; O = 8-amino-3,6-dioxaoctanoic acid (O-spacer unit)

The syntheses were performed in 10 μmole scale starting with N-α-t-Boc-ε-Fmoc-lysine MBHA-PS resin, which was swollen in DCM for about 2 hours. Then, the Boc-protecting group was removed and the PNA part of the conjugate, which contains two extra Lys at the C-terminus, was assembled by automated synthesis using Boc-chemistry. After PNA synthesis, the N-terminal Boc protection was left intact, while the ε-Fmoc protection of the C-terminal lysine bridging unit was cleaved with 20% piperidine in DMF to synthesize the peptide parts of the conjugated oligomeric compounds, which was carried out by manual synthesis in custom fabricated glass columns using Fmoc chemistry. After completion of the synthesis, the N-terminal Fmoc groups were removed and the conjugated oligomeric com- NH functionalities are reprotected by an extended acetylation step using acetic anhydride. Then, after extensive acetylation and removal of $R^2$, a DMT-protected spacer unit (e.g. DMT-O-γ-butyric acid) is introduced. The resin is placed in a synthesis column suitable for oligonucleotide synthesis on the 394 DNA/RNA Synthesizer and the oligonucleotide part of the conjugated oligomeric compound is synthesized by standard phosphoramidite chemistry. Deprotection, purification and analysis of the oligonucleotides are performed as outlined under General Procedures. The following oligonucleotide-peptide conjugates are synthesized using with the above outlined strategy on HMBA-PS supports loaded with the branched bridging units (9–14):

| Name | Sequence N→C | | Modification | $MW_{calc.}$ |
|---|---|---|---|---|
| 116847-KFF | <u>CTG CTA</u> GCC TCT GGA <u>TTT GA</u>-X-Y KFFKFFKFFK | (SEQ ID NO: 3) | _ = 2'-MOE; X = γ-hydroxybutyryl Y = branched linking unit | 9239.6 |
| 116847 PTD-5 | <u>CTG CTA</u> GCC TCT GGA <u>TTT GA</u>-X-Y YARAARRAARR | (SEQ ID NO: 4) | _ = 2'-MOE; X = γ-hydroxybutyryl Y = branched linking unit | 9143.4 |

Example 19

Extending the System to a Trivalent Bridging Unit for Synthesis of PNA-peptide and Oligonucleotide-peptide Conjugates, which are Further Modified by a Target Molecule Using the different amino protecting groups described above, a trivalent bridging unit, e.g. based on cholic acid, as described by Zhou, X.-T., Rehman, A., Li, C., Savage, P. B. (2000) *Org. Lett.*, 2, 3015–3018, can be utilized for the synthesis of PNA and oligonucleotide conjugated oligomeric compounds, to introduce an additional functionality (See FIG. 4). This can be, for example, a target molecule for cancer cells (e.g. folic acid) or other cell types, which can be targeted by a specific membrane receptor. An example is the ASGP-receptor located on hepatocytes, which can be targeted by glycoconjugates. Ashwell, G. and Harford, J. (1982) *Annu. Rev. Biochem.* 51, 531–554; Lee, Y. C., Townsend, R. R., Hardy, M. R., Lonngren, J., Arnarp, J., Haraldsson, M. and Lonn, H. (1983) *J. Biol. Chem.* 258, 199–202; Kawaguchi, K., Kuhlenschmidt, M., Roseman, S. and Lee, Y. C. (1981) *J. Biol. Chem.* 256, 2230–2234; Biessen, E. A. L., Beuting, D. M., Roelen, H. C. P. F., van de Marel, G. A., Van Boom, J. H. and Van Berkel, T. J. C. (1995) *J. Med. Chem.* 38, 1538–1546.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

We claim:

1. A method of preparing a conjugated oligomeric compound comprising the steps of:
   providing a bridging unit bound to a support medium, said bridging unit comprising at least two orthogonally protected amino groups;
   deblocking one of said at least two orthogonally protected amino groups and covalently attaching a conjugate group to said deblocked amino group;
   deblocking another of said at least two orthogonally protected amino groups and covalently attaching a spacer unit comprising a protected hydroxyl group to said another deblocked amino group;
   deprotecting said protected hydroxyl group; and
   covalently attaching an oligomeric compound
   wherein said spacer unit is γ-butyric acid,

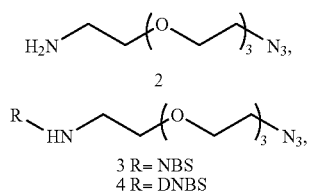

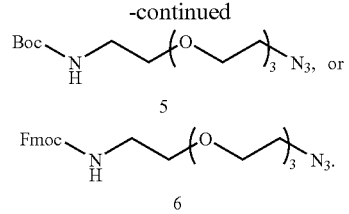

2. The method of claim 1 wherein said covalently attaching step is carried out iteratively.

3. The method of claim 1 further comprising the step of treating said conjugated oligomeric compound with a reagent effective to cleave said conjugated oligomeric compound from said support medium.

4. The method of claim 1 further comprising the step of treating said conjugated oligomeric compound with a reagent effective to remove protecting groups from said conjugated oligomeric compound.

5. The method of claim 1 wherein said oligomeric compound is an oligonucleotide, modified oligonucleotide, oligonucleotide analog or an oligonucleoside.

6. The method of claim 5 wherein said oligomeric compound is iteratively synthesized using phosphoramidite chemistry.

7. The method of claim 5 wherein said oligomeric compound is a hemimer, gapmer or inverted gapmer.

8. The method of claim 1 wherein said conjugate group is selected from a receptor targeting moiety, intercalator, reporter molecule, crosslinking agent, cholesterol, peptide, polypeptide, polyamide, polyamine, amphipathic moiety, polyether, polycation group, lipophilic carrier, protein binder, carbohydrate, a carbohydrate cluster, or a vitamin.

9. The method of claim 8 wherein said conjugate group is cholesterol, folic acid, a peptide, a polypeptide, ibuprofen, biotin or polyethyleneglycol.

10. The method of claim 8 wherein said conjugate group is a peptide or a polypeptide.

11. The method of claim 8 wherein said conjugate group is a peptide and said peptide has a higher percentage of arginine than any other amino acid.

12. The method of claim 1 wherein said bridging unit comprises a moiety derived lysine, 2-substituted malonodiamide, trisubstituted benzene, 3-hydroxyglutaric acid diamide, substituted iminodiacetic acid, or a molecule of Formula X:

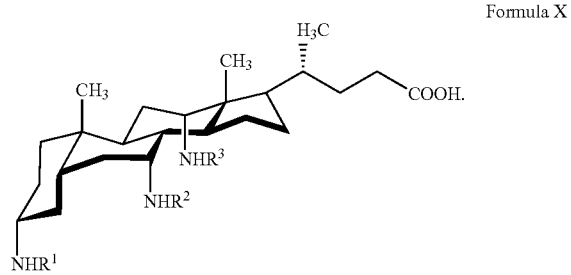

Formula X

13. The method of claim 1 wherein said bridging unit is free of a moiety of the structure:

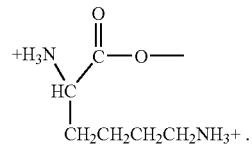

14. The method of claim 1 wherein said bridging unit is bound to said support medium by a linking unit.

15. The method of claim 14 wherein said linking unit is a moiety derived from 5-(4'-aminomethyl-3',5'-dimethoxyphenoxy)valeric acid, 9-amino-xanthen-3-yloxy, thioester, trityl, 4-hydroxymethylbenzoic acid, or a methylbenzhydrylamine.

16. The method of claim 1 wherein said a bridging unit comprises at least three orthogonally protected amino groups.

17. The method of claim 16 further comprising the steps of deblocking the third of said at least three orthogonally protected amino groups and then covalently attaching a conjugate group or an oligomeric compound to said deblocked third amino group.

18. The method of claim 17 further comprising the step of attaching a spacer unit to said deblocked third amino group and then covalently attaching said oligomeric compound to said spacer unit
wherein said spacer units γ-butyric acid,

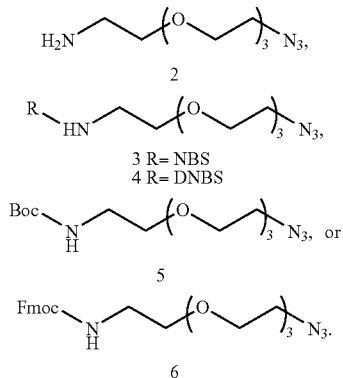

19. The method of claim 18 wherein said spacer unit is derived from tetraalkylene glycol.

* * * * *

UNITED STATES PATENT AND TRADEMARK OFFICE
CERTIFICATE OF CORRECTION

PATENT NO. : 7,038,037 B2
APPLICATION NO. : 10/176419
DATED : May 2, 2006
INVENTOR(S) : Martin A. Maier et al.

It is certified that error appears in the above-identified patent and that said Letters Patent is hereby corrected as shown below:

1) Column 58, Claim 18, line 22, please delete "units" and insert therefore --unit is --.

Signed and Sealed this

Eighth Day of August, 2006

JON W. DUDAS
*Director of the United States Patent and Trademark Office*

SEQUENCE LISTING

```
<160> NUMBER OF SEQ ID NOS: 8

<210> SEQ ID NO 1
<211> LENGTH: 10
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc feature
<222> LOCATION: (1)..(5)
<223> OTHER INFORMATION: Xaa is pseudoisocytosine
<220> FEATURE:
<221> NAME/KEY: misc feature
<222> LOCATION: (8)..(9)
<223> OTHER INFORMATION: Xaa is pseudoisocytosine
<220> FEATURE:
<221> NAME/KEY: misc feature
<222> LOCATION: (11)..(13)
<223> OTHER INFORMATION: Xaa is 8-amino-3, 6-dioxaoctanoic acid
       (O-spacer unit)

<400> SEQUENCE: 1

Xaa Xaa Xaa Xaa Xaa Thr Thr Xaa Xaa Thr
1               5                   10

<210> SEQ ID NO 2
<211> LENGTH: 23
<212> TYPE: PRT
<213> ORGANISM: Artificial Sequence
<220> FEATURE:
<223> OTHER INFORMATION: Synthetic peptide sequence
```

```
<400> SEQUENCE: 2

Thr Cys Cys Thr Thr Cys Cys Cys Cys Lys Lys Lys Lys Phe Phe
1               5                   10                  15

Lys Phe Phe Lys Phe Phe Lys
            20

<210> SEQ ID NO 3
<211> LENGTH: 10
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc feature
<222> LOCATION: (1)..(5)
<223> OTHER INFORMATION: Xaa is pseudoisocytosine
<220> FEATURE:
<221> NAME/KEY: misc_feature
<222> LOCATION: (8)..(9)
<223> OTHER INFORMATION: Xaa is pseudoisocytosine

<400> SEQUENCE: 3

Xaa Xaa Xaa Xaa Xaa Thr Thr Xaa Xaa Thr
1               5                   10

<210> SEQ ID NO 4
<211> LENGTH: 29
<212> TYPE: PRT
<213> ORGANISM: Artificial Sequence
<220> FEATURE:
<223> OTHER INFORMATION: Synthetic peptide sequence

<400> SEQUENCE: 4

Thr Cys Cys Thr Thr Cys Cys Cys Cys Lys Lys Lys Arg Gln Ile
1               5                   10                  15

Lys Ile Trp Phe Gln Asn Arg Arg Met Lys Trp Lys Lys
            20                  25

<210> SEQ ID NO 5
<211> LENGTH: 20
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc feature
<222> LOCATION: (1)..(5)
<223> OTHER INFORMATION: 2'MOE
<220> FEATURE:
<221> NAME/KEY: misc feature
<222> LOCATION: (16)..(20)
<223> OTHER INFORMATION: 2'MOE

<400> SEQUENCE: 5

Cys Thr Gly Cys Thr Ala Gly Cys Cys Thr Cys Thr Gly Gly Ala Thr
1               5                   10                  15

Thr Thr Gly Ala
            20

<210> SEQ ID NO 6
<211> LENGTH: 10
<212> TYPE: PRT
<213> ORGANISM: Artificial Sequence
<220> FEATURE:
<223> OTHER INFORMATION: Synthetic peptide sequence
```

```
<400> SEQUENCE: 6

Lys Phe Phe Lys Phe Phe Lys Phe Phe Lys
1               5                   10

<210> SEQ ID NO 7
<211> LENGTH: 20
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(5)
<223> OTHER INFORMATION: 2'-MOE
<220> FEATURE:
<221> NAME/KEY: misc feature
<222> LOCATION: (16)..(20)
<223> OTHER INFORMATION: 2'-MOE

<400> SEQUENCE: 7

Cys Thr Gly Cys Thr Ala Gly Cys Cys Thr Cys Thr Gly Gly Ala Thr
1               5                   10                  15

Thr Thr Gly Ala
            20

<210> SEQ ID NO 8
<211> LENGTH: 11
<212> TYPE: PRT
<213> ORGANISM: Artificial Sequence
<220> FEATURE:
<223> OTHER INFORMATION: Synthetic peptide sequence

<400> SEQUENCE: 8

Tyr Ala Arg Ala Ala Arg Arg Ala Ala Arg Arg
1               5                   10
```